(12) United States Patent
Llanos et al.

(10) Patent No.: US 6,746,773 B2
(45) Date of Patent: Jun. 8, 2004

(54) COATINGS FOR MEDICAL DEVICES

(75) Inventors: Gerard H. Llanos, Stewartsville, NJ (US); Pallassana Narayanan, Belle Mead, NJ (US); Mark B. Roller, North Brunswick, NJ (US); Angelo Scopelianos, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/962,292

(22) Filed: Sep. 25, 2001

(65) Prior Publication Data

US 2002/0094440 A1 Jul. 18, 2002

Related U.S. Application Data

(63) Continuation-in-part of application No. 09/675,882, filed on Sep. 29, 2000, now abandoned.

(51) Int. Cl.$^7$ .............................................. B23B 27/00
(52) U.S. Cl. ................ 428/421; 604/890.1; 604/891.1; 604/265; 623/1.42; 623/1.43; 623/1.44; 623/1.49
(58) Field of Search ........................... 604/891.1, 890.1, 604/265; 623/1.42, 1.44, 1.43, 1.49; 523/105, 112, 113; 525/937; 524/546; 428/421, 422

(56) References Cited

U.S. PATENT DOCUMENTS

| | | | |
|---|---|---|---|
| 3,051,677 A | | 8/1962 | Rexford |
| 3,779,805 A | | 12/1973 | Alsberg |
| 4,413,359 A | * | 11/1983 | Akiyama et al. ................. 3/1 |
| 4,423,183 A | * | 12/1983 | Close ......................... 524/546 |
| 4,733,665 A | | 3/1988 | Palmaz |
| 4,749,585 A | | 6/1988 | Greco et al. |
| 4,800,882 A | | 1/1989 | Gianturco |
| 4,871,357 A | | 10/1989 | Hsu et al. |
| 4,876,109 A | | 10/1989 | Mayer et al. |
| 4,886,062 A | | 12/1989 | Wiktor |
| 5,047,020 A | | 9/1991 | Hsu |
| 5,053,048 A | | 10/1991 | Pinchuk |
| 5,176,972 A | * | 1/1993 | Bloom et al. ................. 430/14 |
| 5,185,408 A | | 2/1993 | Tang et al. |
| 5,336,518 A | | 8/1994 | Narayanan et al. |
| 5,342,348 A | | 8/1994 | Kaplan |
| 5,368,566 A | | 11/1994 | Crocker |
| 5,380,299 A | | 1/1995 | Fearnot et al. |
| 5,383,853 A | | 1/1995 | Jung et al. |
| 5,383,928 A | | 1/1995 | Scott et al. |
| 5,403,341 A | | 4/1995 | Solar |
| 5,417,969 A | | 5/1995 | Hsu et al. |
| 5,443,458 A | | 8/1995 | Eury |
| 5,447,724 A | | 9/1995 | Helmus et al. |
| 5,464,650 A | | 11/1995 | Berg et al. |
| 5,545,208 A | | 8/1996 | Wolff et al. |
| 5,569,463 A | | 10/1996 | Helmus et al. |
| 5,575,818 A | | 11/1996 | Pinchuk |
| 5,591,224 A | | 1/1997 | Schwartz et al. |
| 5,604,283 A | * | 2/1997 | Wada et al. ................. 524/236 |
| 5,616,608 A | | 4/1997 | Kinsella et al. |
| 5,632,771 A | | 5/1997 | Boatman et al. |
| 5,632,776 A | | 5/1997 | Kurumatani et al. |
| 5,632,840 A | | 5/1997 | Campbell |
| 5,635,201 A | | 6/1997 | Fabo |
| 5,665,728 A | | 9/1997 | Morris et al. |
| 5,679,400 A | | 10/1997 | Tuch |
| 5,684,061 A | * | 11/1997 | Ohnishi et al. ............. 523/114 |
| 5,691,311 A | | 11/1997 | Maraganore et al. |
| 5,697,967 A | | 12/1997 | Dinh et al. |
| 5,713,949 A | | 2/1998 | Jayaraman |
| 5,716,981 A | | 2/1998 | Hunter et al. |

(List continued on next page.)

FOREIGN PATENT DOCUMENTS

| | | |
|---|---|---|
| DE | 19723723 A | 12/1998 |
| EP | 0 568 310 A1 | 4/1993 |
| EP | 0633032 A | 1/1995 |
| EP | 747069 | 12/1996 |
| EP | 0 815 803 A | 1/1998 |
| EP | 0 950 386 A2 | 4/1999 |
| EP | 0 968 688 A | 1/2000 |
| EP | 1 192 957 A | 4/2002 |
| WO | WO 98/36784 A1 | 2/1998 |
| WO | WO 9808463 A | 3/1998 |
| WO | WO 00/27455 A1 | 11/1999 |
| WO | WO 0038754 A | 7/2000 |
| WO | WO 02/26139 A1 | 9/2001 |
| WO | WO 01/87342 A2 | 11/2001 |
| WO | WO 01/87376 A | 11/2001 |
| WO | WO 02/26281 A | 4/2002 |

OTHER PUBLICATIONS

Encyclopedia of Polymer Science and Engineering, vol. 7: fluorocarbon Elastomers, p. 257–267, Mar. 1989.*
Derwent Acc. No. 1999–025723, abstract of DE 19723723 A1, Dec. 3, 1998.*
PCT International Search Report, PCT/US01/30389, Mar. 11, 2002.
European Search Report EP03254747 dated Dec. 3, 2003.
I. Verweire, E. Schact, B. P. Qiang, K. Wang, I. De Scheerder, "Evaluation of Fluorinated Polymers As Coronary Stent Coating," Journal of Materials Science: Materials in Medicine 11. Apr. 2000.

*Primary Examiner*—Ramsey Zacharia

(57) ABSTRACT

The present invention includes biocompatible coatings and films for use on implantable medical devices and medical devices containing such coatings and films applied to a surface thereof, which coatings/films are present on the device in an amount effective to provide an inert surface to be in contact with body tissue of a mammal upon implantation of the device in the mammal, and contain a film-forming polyfluoro copolymer containing the polymerized residue of a moiety selected from the group consisting of vinylidenefluoride and tetrafluoroethylene copolymerized with a second moiety other than the first moiety, wherein the relative amounts of the polymerized residue of the first and second moieties are effective to provide the coating and films with properties effective for use in coating implantable med devices.

5 Claims, 4 Drawing Sheets

U.S. PATENT DOCUMENTS

| | | |
|---|---|---|
| 5,759,205 A | 6/1998 | Valentini ..................... 623/16 |
| 5,776,184 A | 7/1998 | Tuch |
| 5,824,048 A | 10/1998 | Tuch |
| 5,824,049 A | 10/1998 | Ragheb et al. |
| 5,827,587 A * | 10/1998 | Fukushi ..................... 428/36.6 |
| 5,865,814 A | 2/1999 | Tuch |
| 5,873,904 A | 2/1999 | Ragheb et al. |
| 5,879,697 A | 3/1999 | Ding et al. |
| 5,897,911 A | 4/1999 | Loeffler |
| 5,922,393 A | 7/1999 | Jayaraman |
| 5,932,299 A | 8/1999 | Katoot |
| 6,153,252 A | 11/2000 | Hossainy et al. |

* cited by examiner

Release of Drug from FC-2261Q it would be advantageous to develop coatings for implantable medical devices that will reduce thrombosis, restenosis, or other adverse reactions, that may include, but do not require, the use of pharmaceutical or therapeutic agents or drugs to achieve such affects, and that possess physical and mechanical properties effective for use in such devices, even when such coated devices are subjected to relatively low maximum temperatures.

COATINGS FOR MEDICAL DEVICES

This patent application is a continuation-in-part of U.S. patent application Ser. No. 09/675,882, filed on Sep. 29, 2000, abandoned on Oct. 22, 2002.

FIELD OF THE INVENTION

The invention relates to the use of polyfluoro copolymers as coatings for implantable surgical medical devices.

BACKGROUND OF THE INVENTION

Implantable medical devices are used in various medical procedures. Such devices include, without limitation, stents, catheters, sutures, meshes, vascular grafts, shunts and filters for removing emboli.

Stents, which generally are open tubular structures, have become increasingly important in medical procedures to restore the function of body lumens. Stents now are commonly used in translumenial procedures such as angioplasty to restore adequate blood flow to the heart and other organs. However, deployment of stents may stimulate foreign body reactions thereto that result in thrombosis or restenosis.

To avoid these complications, a variety of stent coatings and compositions have been proposed to reduce the incidence of these complications. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The reported mechanism for delivery of the agent has been via diffusion of the agent through either the bulk polymer, or through pores that are created in the polymer structure, or by erosion of a biodegradable coating.

Both bioabsorbable and biostable compositions have been reported as coatings for stents. They generally have been polymeric coatings that either encapsulate a pharmaceutical/therapeutic agent or drug, e.g. taxol, rapamycin, etc., or bind such an agent to the surface, e.g. heparin-coated stents. These coatings are applied to the stent in a number of ways, including, though not limited to, dip, spray, or spin coating processes.

One class of biostable materials that has been reported as coatings for stents is polyfluoro homopolymers. Polytetrafluoroethylene (PTFE) homopolymers have been used as implants for many years. These homopolymers are not soluble in any solvent at reasonable temperatures and therefore are difficult to coat onto small medical devices while maintaining important features of the devices (e.g. slots in stents).

Stents with coatings made from polyvinylideneflouride homopolymers and containing pharmaceutical/therapeutic agents or drugs for release have been suggested. However, like most crystalline polyfluoro homopolymers, they are difficult to apply as high quality films onto surfaces without subjecting them to relatively high temperatures, e.g. greater than about 125–200° C., that correspond to the melting temperature of the polymer.

It would be advantageous to develop coatings for implantable medical devices that will reduce thrombosis, restenosis, or other adverse reactions, that may include, but do not require, the use of pharmaceutical or therapeutic agents or drugs to achieve such affects, and that possess physical and mechanical properties effective for use in such devices, even when such coated devices are subjected to relatively low maximum temperatures.

SUMMARY OF THE INVENTION

The present invention includes biocompatible coatings and films for use on implantable medical devices and medical devices comprising such coatings and films applied to a surface thereof that is to be in contact with body tissue of a mammal. The biocompatible film provides an inert surface to be in contact with body tissue of a mammal upon implantation of the device in the mammal. The coating and film comprise a film-forming polyfluoro copolymer comprising the polymerized residue of a first moiety selected from the group consisting of vinylidenefluoride (VDF) and tetrafluoroethylene (TFE), and the polymerized residue of a second moiety other than said first moiety and which is copolymerized with said first moiety, thereby producing the polyflouro copolymer, said second moiety being capable of providing toughness or elastomeric properties to the polyfluoro copolymer, wherein the relative amounts of said polymerized residue of said first moiety and said polymerized residue of said second moiety are effective to provide the coating and film produced therefrom with properties effective for use in coating implantable medical devices.

DETAILED DESCRIPTION OF THE INVENTION

Figure 1:
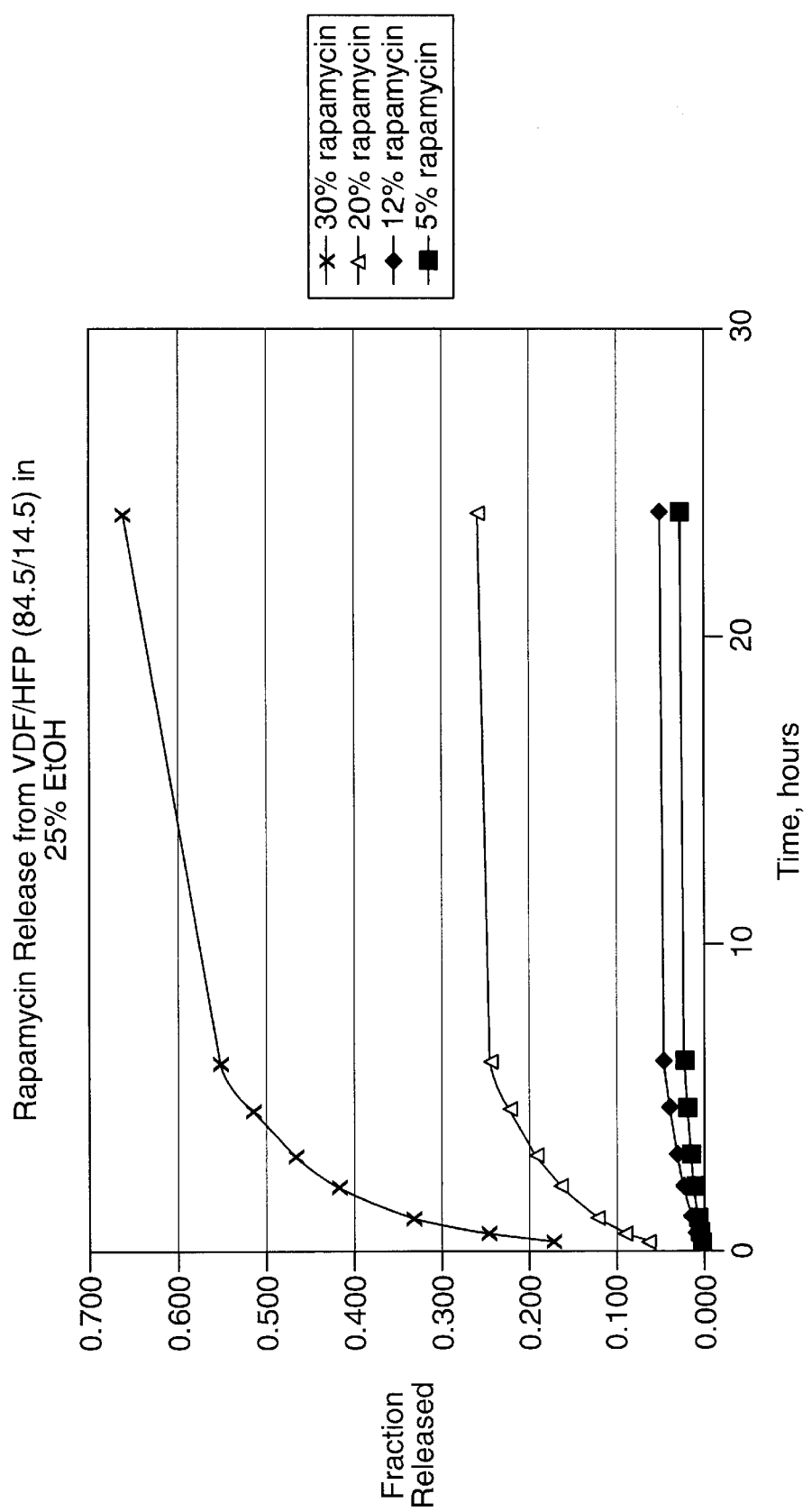
FIG. 1 indicates the fraction of drug released as a function of time from coatings of the present invention over which no topcoat has been disposed.

The present invention provides polymeric coatings comprising a polyfluoro copolymer and implantable medical devices, e.g. stents, coated with a film of the polyfluoro polymeric coating in amounts effective to reduce thrombosis and/or restenosis when such stents are used in, e.g. angioplasty procedures. As used herein, polyfluoro copolymers means those copolymers comprising the polymerized residue of a first moiety selected from the group consisting of vinylidenefluoride and tetrafluoroethylene, the polymerized residue of a second moiety other than the first moiety and which is copolymerized with the first moiety to produce the polyfluoro copolymer, said second moiety being capable of providing toughness or elastomeric properties to the polyfluoro copolymer, wherein the relative amounts of the polymerized residue of the first moiety and the polymerized residue of the second moiety are effective to provide coatings and films made from such polyfluoro copolymers with properties effective for use in coating implantable medical devices.

In certain embodiments, the invention provides an inert, low surface energy coating for medical devices that are implanted into the body of a mammal and later retrieved therefrom. The low surface energy coating makes wetting of the device surface and protein deposition thereon difficult, which could prolong the time for encapsulation in the body, after which time the device could be removed easily.

In certain embodiments of the invention, although not necessary, the coatings may comprise pharmaceutical or therapeutic agents in amounts effective for achieving desired purposes, e.g. for reducing thrombosis or restenosis, and stents coated with such coatings may provide sustained release of the agents. Films prepared from certain polyfluoro copolymer coatings of the present invention provide the physical and mechanical properties required of conventional coated medical devices, even where maximum temperatures to which the device, coatings and films are exposed are limited to relatively low temperatures, e.g. less than about 100° C., preferably at about ambient temperatures. This is particularly important when using the coating/film to deliver pharmaceutical/therapeutic agent or drugs that are heat sensitive, or when applying the coating onto temperature-sensitive devices such as, but not limited to, catheters. When maximum exposure temperature is not an issue, e.g. where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked by standard methods described in, e.g. *Modern Fluoropolymers*, J. Shires editor, John Wiley & Sons, New York, 1997, pp. 77–87.

The present invention comprises polyfluoro copolymers that provide improved biocompatible coatings for medical devices. These coatings provide inert surfaces to be in contact with body tissue of a mammal, e.g. a human, sufficient to reduce thrombosis, or restenosis, or other undesirable reactions. While most reported coatings made from polyfluoro homopolymers are insoluble and/or require high heat, e.g. greater than about 125° C., to obtain films with adequate physical and mechanical properties for use on implantable devices, e.g. stents, or are not particularly tough or elastomeric, films prepared from the polyfluoro copolymer coatings of the present invention provide adequate adhesion, toughness or elasticity, and resistance to cracking when formed on medical devices claimed herein. In certain embodiments, this is the case even where the coated devices are subjected to relatively low maximum temperatures, e.g. less than about 100° C., preferably less than about 65° C., and more preferably about 60° C. or less. In such cases, preferred polyfluoro copolymers may comprise the polymerized residue of from about 65 to about 55 weight percent polymerized residue of the first moiety, e.g. VDF, and from about 35 to about 45 weight percent polymerized residue of the second moiety, e.g. hexafluoropropylene. In certain embodiments, such polyfluoro copolymers will be crystalline, although amorphous copolymers of similar composition also are employed.

The polyfluoro copolymers used for coatings according to the present invention must be film-forming polymers that have molecular weight high enough so as not to be waxy or tacky. The polymers and films formed therefrom must adhere to the stent and not be readily deformable after deposition on the stent as to be able to be displaced by hemodynamic stresses. The polymer molecular weight must be high enough to provide sufficient toughness so that films comprising the polymers will not be rubbed off during handling or deployment of the stent. In certain embodiments the coating will not crack where expansion of the stent or other medical devices, such as vena cava filters, occurs. The flow point of the polymer used in the present invention should be above 40° C., preferably above about 45° C., more preferably above 50° C. and most preferably above 55° C.

Coatings of the present invention comprise polyfluoro copolymers, as defined hereinabove. The second moiety copolymerized with the first moiety to prepare the polyfluoro copolymer may be selected from those biocompatible monomers that would provide biocompatible polymers acceptable for implantation in a mammal, while maintaining sufficient elastomeric film properties for use on medical devices claimed herein. Such monomers include, without limitation, hexafluoropropylene (HFP), tetrafluoroethylene (TFE), VDF, 1-hydropentafluoropropylene, perfluoro (methyl vinyl ether), chlorotrifluoroethylene (CTFE), pentafluoropropene, trifluoroethylene, hexafluoroacetone and hexafluoroisobutylene.

Polyfluoro copolymers used in the present invention typically comprise vinylidinefluoride copolymerized with HFP, in the weight ratio of from about 50 to about 92 weight percent vinylidinefluoride to about 50 to about 8 weight percent HFP. Preferably, polyfluoro copolymers used in the present invention comprise from about 50 to about 85 weight percent VDF copolymerized with from about 50 to about 15 weight percent HFP. More preferably, the polyfluoro copolymers will comprise from about 55 to about 70 weight percent VDF copolymerized with from about 45 to about 30 weight percent HFP. Even more preferably, polyfluoro copolymers comprise from about 55 to about 65 weight percent VDF copolymerized with from about 45 to about 35 weight percent HFP. Such polyfluoro copolymers are soluble, in varying degrees, in solvents such as dimethylacetamide (DMAc), tetrahydrofuran, dimethyl formamide, dimethyl sulfoxide and n-methyl pyrrolidone. Some are soluble in methylethylketone (MEK), acetone, methanol and other solvents commonly used in applying coatings to conventional implantable medical devices.

Conventional polyfluoro homopolymers are crystalline and difficult to apply as high quality films onto metal surfaces without exposing the coatings to relatively high temperatures that correspond to the melting temperature (Tm) of the polymer. The elevated temperature serves to provide films prepared from such PVDF homopolymer coatings that exhibit sufficient adhesion of the film to the device, while preferably maintaining sufficient flexibility to resist film cracking upon expansion/contraction of the coated medical device. Certain films and coatings according to the present invention provide these same physical and mechanical properties, or essentially the same properties, even when the maximum temperatures to which the coatings and films are exposed is less than about 100° C., and preferably less than about 65° C. This is particularly important when the coatings/films comprise pharmaceutical or therapeutic agents or drugs that are heat sensitive, e.g. subject to chemical or physical degradation or other heat-induced negative affects, or when coating heat sensitive substrates of medical devices, e.g. subject to heat-induced compositional or structural degradation.

Depending on the particular device upon which the coatings and films of the present invention are to be applied and the particular use/result required of the device, polyfluoro copolymers used to prepare such devices may be crystalline, semi-crystalline or amorphous.

Where devices have no restrictions or limitations with respect to exposure of same to elevated temperatures, e.g. 100° C. or higher, crystalline polyfluoro copolymers may be employed. Crystalline polyfluoro copolymers tend to resist the tendency to flow under applied stress or gravity when exposed to temperatures above their glass transition (Tg) temperatures. Crystalline polyfluoro copolymers provide tougher coatings and films than their fully amorphous counterparts. In addition, crystalline polymers are more lubricious and more easily handled through crimping and transfer processes used to mount self-expanding stents, e.g. nitinol stents.

Semi-crystalline and amorphous polyfluoro copolymers are advantageous where exposure to elevated temperatures is an issue, e.g. where heat-sensitive pharmaceutical or therapeutic agents are incorporated into the coatings and films, or where device design, structure and/or use preclude exposure to such elevated temperatures. Semi-crystalline polyfluoro copolymer elastomers comprising relatively high levels, e.g. from about 30 to about 45 weight percent of the second moiety, e.g. HFP, copolymerized with the first moiety, e.g. VDF, have the advantage of reduced coefficient of friction and self-blocking relative to amorphous polyfluoro copolymer elastomers. Such characteristics can be of significant value when processing, packaging and delivering medical devices coated with such polyfluoro copolymers. In addition, such polyfluoro copolymer elastomers comprising such relatively high content of the second moiety serves to control the solubility of certain agents, e.g. Sirolimus, in the polymer and therefore controls permeability of the agent through the matrix.

Polyfluoro copolymers utilized in the present inventions may be prepared by various known polymerization methods. For example, high pressure, free-radical, semi-continuous emulsion polymerization techniques such as those disclosed in *Fluoroelastomers-dependence of relaxation phenomena on composition*, POLYMER 30, 2180, 1989, by Ajroldi, et al, may be employed to prepare amorphous polyfluoro copolymers, some of which may be elastomers. In addition, free-radical batch emulsion polymerization techniques disclosed herein may be used to obtain polymers that are semi-crystalline, even where relatively high levels of the second moiety, e.g. greater than about 19–20 mole percent (equivalent to about 36–37 weight percent), are included.

One embodiment of the invention comprises stents coated with a film of a polyfluoro copolymer according to the present invention. Conventional stents are used in translumenial procedures such as angioplasty to restore adequate blood flow to the heart and other organs. They generally are cylindrical and perforated with passages that are slots, ovoid, circular or the like shape. Stents also may be composed of helically wound or serpentine wire structures in which the spaces between the wires form passages. Stents may be flat perforated structures that are subsequently rolled to form tubular or cylindrical structures that are woven, wrapped, drilled, etched or cut to form passages. Examples of stents that may be advantageously coated by polyfluoro copolymers of the present invention include, but are not limited to, stents described in U.S. Pat. Nos. 4,733,665; 4,800,882; 4,886,062, 5,514,154, and 6,190,403, the contents each of which is incorporated herein in its entirety as if set forth herein. These stents can be made of biocompatible materials, including biostable and bioabsorbable materials. Suitable biocompatible metals include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and blends thereof).

The film-forming biocompatible polymer coatings generally are applied to the stent in order to reduce local turbulence in blood flow through the stent, as well as adverse tissue reactions. The coatings and films formed therefrom also may be used to administer a pharmaceutically active material to the site of the stent placement. Generally, the amount of polymer coating to be applied to the stent will vary depending on, among other possible parameters, the particular polyfluoro copolymer used to prepare the coating, the stent design and the desired effect of the coating. Generally, the coated stent will comprise from about 0.1 to about 15 weight percent of the coating, preferably from about 0.4 to about 10 weight percent. The polyfluoro copolymer coatings may be applied in one or more coating steps, depending on the amount of polyfluoro copolymer to be applied. Different polyfluoro copolymers may be used for different layers in the stent coating. In fact, in certain embodiments, it is highly advantageous to use a diluted first coating solution comprising a polyfluoro copolymer as a primer to promote adhesion of a subsequent polyfluoro copolymer coating layer that may contain pharmaceutically active materials. The individual coatings may be prepared from different polyfluoro copolymers.

Additionally, a top coating can be applied to delay release of the pharmaceutical agent, or they could be used as the matrix for the delivery of a different pharmaceutically active material. Layering of coatings can be used to stage release of the drug or to control release of different agents placed in different layers.

Blends of polyfluoro copolymers also may be used to control the release rate of different agents or to provide desirable balance of coating properties, i.e. elasticity, toughness, etc., and drug delivery characteristics, e.g. release profile. Polyfluoro copolymers with different solubilities in solvents can be used to build up different polymer layers that may be used to deliver different drugs or to control the release profile of a drug. For example, polyfluoro copolymers comprising 85.5/14.5 (wt/wt) of poly(VDF/HFP) and 60.6/39.4 (wt/wt) of poly(VDF/HFP) are both soluble in DMAc. However, only the 60.6/39.4 poly(VDF/HFP) polyfluoro copolymer is soluble in methanol.

So, a first layer of the 85.5/14.5 poly(VDF/HFP) polyfluoro copolymer comprising a drug could be over-coated with a topcoat of the 60.6/39.4 poly(VDF/HFP) polyfluoro copolymer made with the methanol solvent. The top coating can be used to delay the drug deliver of the drug contained in the first layer. Alternatively, the second layer could contain a different drug to provide for sequential drug delivery. Multiple layers of different drugs could be provided by alternating layers of first one polyfluoro copolymer, then the other. As will be readily appreciated by those skilled in the art numerous layering approaches can be used to provide the desired drug delivery.

The coatings can be used to deliver therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); Angiogenic agents: vascular endothelial growth factor (VEGF), fibroblast growth factor (FGF); nitric oxide donors; cell cycle inhibitors; mTOR inhibitors; growth factor signal transduction knase inhibitors; anti-sense oligonucleotide; prodrug molecules; and combinations thereof.

Coatings may be formulated by mixing one or more therapeutic agents with the coating polyfluoro copolymers in a coating mixture. The therapeutic agent may be present as a liquid, a finely divided solid, or any other appropriate physical form. Optionally, the coating mixture may include one or more additives, e.g., nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a polyfluoro copolymer coating to modify the release profile. Appropriate relative amounts can be determined by monitoring the in vitro and/or in vivo release profiles for the therapeutic agents.

The best conditions for the coating application are when the polyfluoro copolymer and pharmaceutic agent have a common solvent. This provides a wet coating that is a true solution. Less desirable, yet still usable, are coatings that contain the pharmaceutical agent as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that need to remain essentially free of coating. In cases where a dispersion is applied to the stent and the smoothness of the coating film surface requires improvement, or to be ensured that all particles of the drug are fully encapsulated in the polymer, or in cases where the release rate of the drug is to be slowed, a clear (polyfluoro copolymer only) topcoat of the same polyfluoro copolymer used to provide sustained release of the drug or another polyfluoro copolymer that further restricts the diffusion of the drug out of the coating can be applied. The topcoat can be applied by dip coating with mandrel to clear the slots, referred to herein as the dip and wipe method. This method is disclosed in U.S. Pat. No. 6,153,252, the contents of which are incorporated herein in their entirety. Other methods for applying the topcoat include spin coating and spray coating. Dip coating of the top coat can be problematic if the drug is very soluble in the coating solvent, which swells the polyfluoro copolymer, and the clear coating solution acts as a zero concentration sink and redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001% to about 70%, more typically about 0.001% to about 60%.

The quantity and type of polyfluoro copolymers employed in the coating film containing the pharmaceutic agent will vary depending on the release profile desired and the amount of drug employed. The product may contain blends of the same or different polyfluoro copolymers having different molecular weights to provide the desired release profile or consistency to a given formulation.

Polyfluoro copolymers may release dispersed drug by diffusion. This can result in prolonged delivery (over, say 1 to 2,000 hours, preferably 2 to 800 hours) of effective amounts (say, 0.001 $\mu g/cm^2$-min to 100 $\mu g/cm^2$-min) of the drug. The dosage can be tailored to the subject being treated, the severity of the affliction, the judgment of the prescribing physician, and the like. Individual formulations of drugs and polyfluoro copolymers may be tested in appropriate in vitro and in vivo models to achieve the desired drug release profiles. For example, a drug could be formulated with a polyfluoro copolymer, or blend of polyfluoro copolymers, coated onto a stent and placed in an agitated or circulating fluid system, e.g. 25% ethanol in water. Samples of the circulating fluid could be taken to determine the release profile (such as by HPLC, UV analysis or use of radiotagged molecules). The release of a pharmaceutical compound from a stent coating into the interior wall of a lumen could be modeled in appropriate animal system. The drug release profile could then be monitored by appropriate means such as, by taking samples at specific times and assaying the samples for drug concentration (using HPLC to detect drug concentration). Thrombus formation can be modeled in animal models using the $^{111}$In-platelet imaging methods described by Hanson and Harker, Proc. Natl. Acad. Sci. USA 85:3184–3188 (1988). Following this or similar procedures, those skilled in the art will be able to formulate a variety of stent coating formulations.

While not a requirement of the present invention, the coatings and films may be crosslinked once applied to the medical devices. Crosslinking may be affected by any of the known crosslinking mechanisms, such as chemical, heat or light. In addition, crosslinking initiators and promoters may be used where applicable and appropriate. In those embodiments utilizing crosslinked films comprising pharmaceutical agents, curing may affect the rate at which the drug diffuses from the coating. Crosslinked polyfluoro copolymers films and coatings of the present invention also may be used without drug to modify the surface of implantable medical devices.

EXAMPLES

Example 1

A poly(VDF) homopolymer (Solef 1008 from Solvay Advanced Polymers, Houston, Tex., Tm about 175° C.) and polyfluoro copolymers of poly(VDF/HFP), 92/8 and 91/9 weight percent VDF/HFP, respectively, as determined by $F^{19}$ NMR (eg: Solef 11010 and 11008, Solvay Advanced Polymers, Houston, Tex., Tm about 159° C. and 160° C., respectively) were examined as potential coatings for stents. These polymers are soluble in solvents such as, but not limited to, DMAc, N,N-dimethylformamide (DMF), dimethyl sulfoxide (DMSO), N-methylpyrrolidone (NMP), tetrahydrofuran (THF) and acetone. Polymer coatings were prepared by dissolving the polymers in acetone, at 5 weight percent as a primer, or by dissolving the polymer in 50/50 DMAc/acetone, at 30 weight percent as a topcoat. Coatings that were applied to the stents by dipping and dried at 60° C. in air for several hours, followed by 60° C. for 3 hours in a <100 mm Hg vacuum, resulted in white foamy films. As applied, these films adhered poorly to the stent and flaked off, indicating they were too brittle. When stents coated in this manner were heated above 175° C., i.e. above the melting temperature of the polymer, a clear, adherent film was formed. Such coatings require high temperatures, e.g. above the melting temperature of the polymer, to achieve high quality films.

Example 2

A polyfluoro copolymer (Solef 21508) comprising 85.5 weight percent VDF copolymerized with 14.5 weight percent HFP, as determined by $F^{19}$ NMR, was evaluated. This copolymer is less crystalline than the polyfluoro homopolymer and copolymers described in Example 1. It also has a lower melting point reported to be about 133° C. Once again, a coating comprising about 20 weight percent of the polyfluoro copolymer was applied from a polymer solution in 50/50 DMAc/MEK. After drying (in air) at 60° C. for several hours, followed by 60° C. for 3 hours in a <100 mtorr Hg vacuum, clear adherent films were obtained. This eliminated the need for a high temperature heat treatment to achieve high quality films. Coatings were smoother and more adherent than those of Example 1. Some coated stents that underwent expansion show some degree of adhesion loss and "tenting" as the film pulls away from the metal. Where necessary, modification of coatings containing such copolymers may be made, e.g. by addition of plasticizers or the like to the coating compositions. Films prepared from such coatings may be used to coat stents or other medical devices, particularly where those devices are not susceptible to expansion to the degree of the stents.

The coating process above was repeated, this time with a coating comprising the 85.5/14.6 (wt/wt) (VDF/HFP) and about thirty (30) weight percent of rapamycin (Wyeth-Ayerst Laboratories, Philadelphia, Pa.), based on total weight of coating solids. Clear films that would occasionally crack or peel upon expansion of the coated stents resulted. It is believed that inclusion of plasticizers and the like in the coating composition will result in coatings and films for use on stents and other medical devices that are not susceptible to such cracking and peeling.

Example 3

Polyfluoro copolymers of still higher HFP content then were examined. This series of polymers were not semi-crystalline, but rather are marketed as elastomers. One such copolymer is Fluorel FC-2261Q (from Dyneon, a 3M-Hoechst Enterprise, Oakdale, Minn.), a 60.6/39.4 (wt/wt) copolymer of VDF/HFP. Although this copolymer has a Tg well below room temperature (Tg about −20° C.), it is not tacky at room temperature or even at 60° C. This polymer has no detectable crystallinity when measured by Differential Scanning Calorimetry (DSC) or by wide angle X-ray diffraction. Films formed on stents as described above were non-tacky, clear, and expanded without incident when the stents were expanded.

The coating process above was repeated, this time with coatings comprising the 60.6/39.4 (wt/wt) poly(VDF/HFP) and about nine (9), thirty (30) and fifty (50) weight percent of rapamycin , based on total weight of coating solids, respectively. Coatings comprising about 9 and 30 weight percent rapamycin provided white, adherent, tough films that expanded without incident on the stent. Inclusion of 50% drug, in the same manner, resulted in some loss of adhesion upon expansion.

Changes in the comonomer composition of the polyfluoro copolymer also can affect the nature of the solid state coating, once dried. For example, the semi-crystalline copolymer, Solef 21508, containing 85.5% VDF polymerized with 14.5% by weight HFP forms homogeneous solutions with about 30% rapamycin (drug weight divided by total solids weight, e.g. drug plus copolymer) in DMAc and 50/50 DMAc/MEK. When the film is dried (60° C./16 hours followed by 60° C./3 hours in vacuum of 100 mm Hg) a clear coating, indicating a solid solution of the drug in the polymer, is obtained. Conversely, when an amorphous copolymer, Fluorel FC-2261Q, of poly(VDF/HFP) at 60.6/39.5 (wt/wt) forms a similar 30% solution of rapamycin in DMAc/MEK and is similarly dried, a white film, indicating phase separation of the drug and the polymer, is obtained. This second drug containing film is much slower to release the drug into an in vitro test solution of 25% ethanol in water than is the former clear film of crystalline Solef 21508. X-ray analysis of both films indicates that the drug is present in a non-crystalline form. Poor or very low solubility of the drug in the high HFP-containing copolymer results in slow permeation of the drug through the thin coating film. Permeability is the product of diffusion rate of the diffusing species (in this case the drug) through the film (the copolymer) and the solubility of the drug in the film.

Example 4
In Vitro Release Results of Rapamycin from Coating

Figure 2:
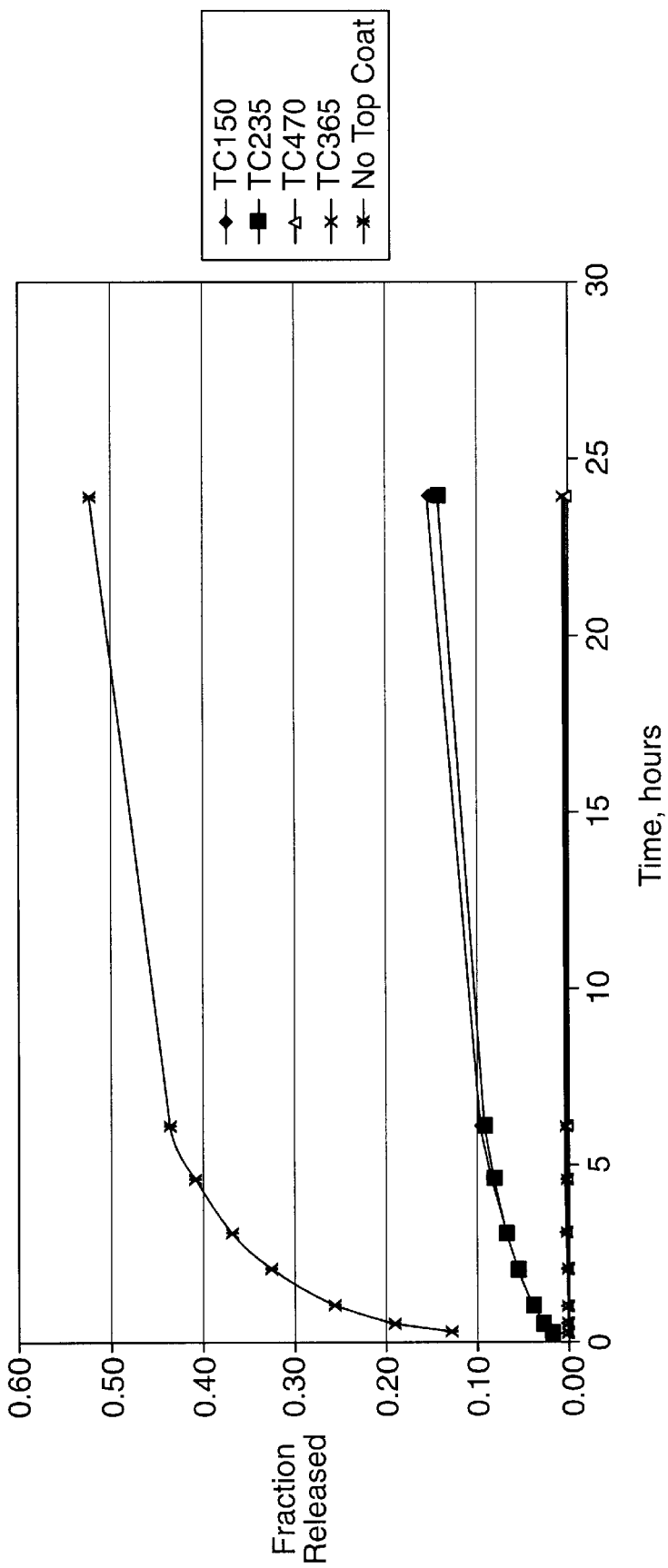
FIG. 2 indicates the fraction of drug released as a function of time from coatings of the present invention including a topcoat disposed thereon.
Figure 3:
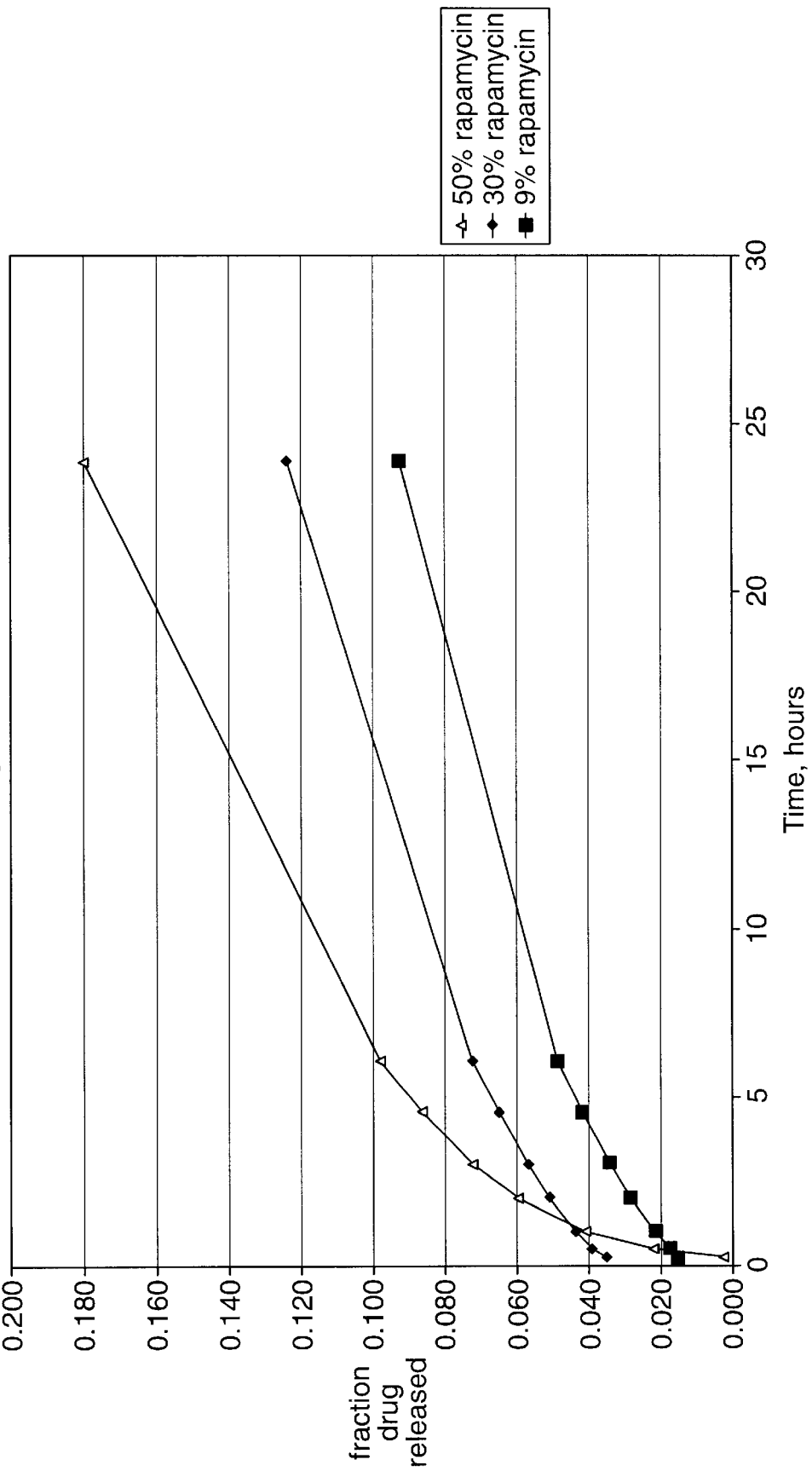
FIG. 3 indicates the fraction of drug released as a function of time from coatings of the present invention over which no topcoat has been disposed.

FIG. 1 is a plot of data for the 85.5/14.5 VDF/HFP polyfluoro copolymer, indicating fraction of drug released as a function of time, with no topcoat. FIG. 2 is a plot of data for the same polyfluoro copolymer over which a topcoat has been disposed, indicating that most effect on release rate is with a clear topcoat. As shown therein, TC150 refers to a device comprising 150 micrograms of topcoat, TC235 refers to 235 micrograms of topcoat, etc. The stents before top coating had an average of 750 micrograms of coating containing 30% rapamycin (based on drug/[drug+polymer]) FIG. 3 is a plot for the 60.6/39.4 VDF/HFP polyfluoro copolymer, indicating fraction of drug released as a function of time, showing significant control of release rate from the coating without the use of a topcoat. Release is controlled by loading of drug in the film.

Example 5
In Vivo Stent Release Kinetics of Rapamycin from Poly (VDF/HFP)

Nine (9) New Zealand white rabbits (2.5–3.0 kg) on a normal diet were given aspirin 24 hours prior to surgery, again just prior to surgery and for the remainder of the study. At the time of surgery, animals were premedicated with Acepromazine (0.1–0.2 mg/kg) and anesthetized with a Ketamine/Xylazine mixture (40 mg/kg and 5 mg/kg, respectively). Animals were given a single intraprocedural dose of heparin (150 IU/kg, i.v.).

Arteriectomy of the right common carotid artery was performed and 5 F catheter introducer (Cordis, Inc.) placed in the vessel and anchored with ligatures. Iodine contrast agent was injected to visualize the right common carotid artery, brachiocephalic trunk and aortic arch. A steerable guide wire (0.014 inch/180 cm, Cordis, Inc.) was inserted via the introducer and advanced sequentially into each iliac artery to a location where the artery possesses a diameter closest to 2 mm using the angiographic mapping done previously. Two stents coated with a film made from poly (VDF/HFP):(60.6/39.4), with about 30% rapamycin(based on drug/[drug+polymer]) were deployed in each animal where feasible, one in each iliac artery, using 3.0 mm balloon and inflation to 8–10 ATM for 30 seconds followed after a 1 minute interval by a second inflation to 8–10 ATM for 30 seconds. Follow-up angiographs visualizing both iliac arteries are obtained to confirm correct deployment position of the stent.

At the end of procedure, the carotid artery was ligated and the skin is closed with 3/0 vicryl suture using a one layered interrupted closure. Animals were given butoropanol (0.4 mg/kg, s.c.) and gentamycin (4 mg/kg, i.m.). Following recovery, the animals were returned to their cages and allowed free access to food and water.

Figure 4:
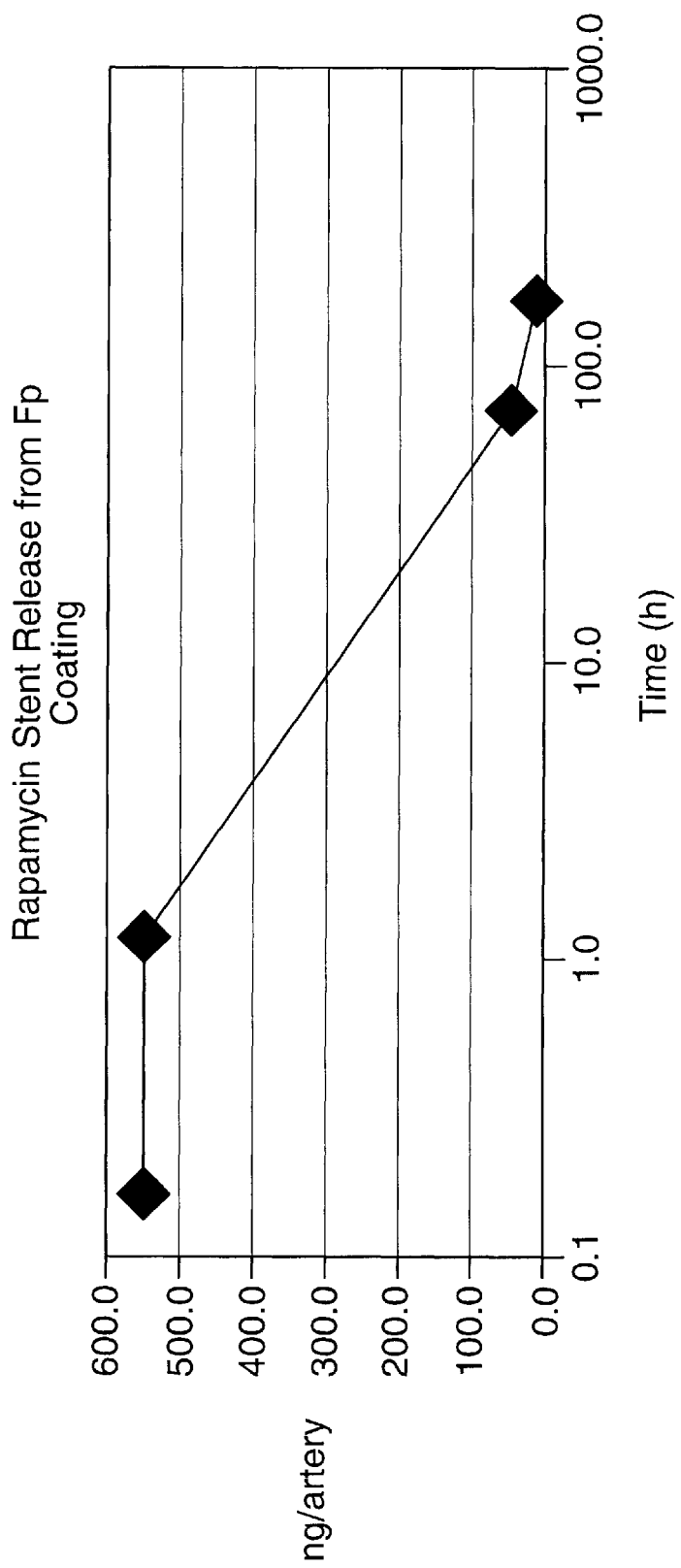
FIG. 4 indicates in vivo stent release kinetics of rapamycin from poly(VDF/HFP).

Due to early deaths and surgical difficulties, 2 animals were not used in this analysis. Stented vessels were removed from the remaining 7 animals at the following time points: 1 vessel (1 animal) at 10 min post implant; 6 vessels (3 animals) between 45 min and 2 h post-implant (average, 1.2 hours); 2 vessels (2 animals) at 3 d post implant; and 2 vessels (1 animal) at 7 d post-implant. In one animal at 2 hours, the stent was retrieved from the aorta rather than the iliac artery. Upon removal, arteries were carefully trimmed at both the proximal and distal ends of the stent. Vessels were then carefully dissected free of the stent, flushed to remove any residual blood, and both stent and vessel frozen immediately, wrapped separately in foil, labeled and kept frozen at −80° C. When all samples had been collected, vessels and stents were frozen, transported and subsequently analyzed for rapamycin in tissue. Results are shown in FIG. 4.

Example 6

Purifying the Polymer

The Fluorel FC-2261Q copolymer was dissolved in MEK at about 10 weight percent and was washed in a 50/50 mixture of ethanol/water. The (ethanol/water): MEK solution ratio=about 14:1. The polymer precipitated out and was separated from the solvent phase by centrifugation. The polymer again was dissolved in MEK and the washing procedure repeated. The polymer was dried after each washing step at 60° C. in a vacuum oven (<200 mtorr) over night.

Example 7

In Vivo Testing of Coated Stents in Porcine Coronary Arteries

CrossFlex® stents (available from Cordis, a Johnson & Johnson Company) were coated with the "as received" Fluorel FC-2261Q PVDF copolymer and with the purified polyfluoro copolymer of example 6, using the dip and wipe approach. The coated stents were sterilized using ethylene oxide and a standard cycle. The coated stents and bare metal stents (controls) were implanted in porcine coronary arteries, where they remained for 28 days.

Angiography was performed on the pigs at implantation and at 28 days. Angiography indicated that the control uncoated stent exhibited about 21 percent restenosis. The polyfluoro copolymer "as received" exhibited about 26% restenosis (equivalent to the control) and the washed copolymer exhibited about 12.5% restenosis.

Histology results reported neointimal area at 28 days to be 2.89±0.2, 3.57±0.4 and 2.75±0.3, respectively, for the bare metal control, the unpurified copolymer and the purified copolymer.

Example 8

Utilizing the following high pressure, free-radical batch emulsion polymerization technique, a series of semi-crystalline, poly(VDF/HFP) copolymer elastomers was prepared.

The VDF and HFP monomers were premixed under pressure in a pressure vessel. HPLC-grade water, surfactant and initiator were mixed outside of a 2 liter Zipperclave® reactor (Autoclave Engineers, Erie, Pa.) and then charged to the reactor, which then was sealed. The premixed monomers then were transferred under nitrogen pressure to the reactor. While stirring, the reactor was raised to the desired temperature and held for a predetermined period of time. The reactor then was cooled and residual monomer vented. The resultant polymer latex was removed from the reactor and coagulated or crashed by adding dilute hydrochloric acid, followed by aqueous sodium chloride. The resulting polymer was washed extensively with water and dried.

The polyfluoro copolymers then were compared with respect to kinetic coefficient of friction of a film prepared therefrom to the kinetic coefficient of friction of a film prepared from a commercial amorphous polyfluoro copolymer comprising 59.5 weight percent VDF copolymerized with 40.5 weight percent HFP utilizing the following procedure.

A 57.2 mm wide by 140.0 mm long polymer film was cast on a 101.6 mm wide by 203.2 mm long aluminum panel (Q-panel, anodized finish, A-48). A silicone rubber gasket was placed on the aluminum panel and clamped using binder clips. The mold was leveled in a fume hood using a bubble level. Approximate 5.0 g of 10.0% polymer solution in methyl ethyl ketone was poured into the mold slowly. The film was dried at room temperature for 3 days followed by 3 hours at 23° C. and 50% R.H. prior to testing.

The kinetic coefficient of friction of the polymer film was measured in accordance with the method described in ASTM D 1894-00, "Static and Kinetic Coefficients of Friction of Plastic Film and Sheeting", Method C. A 46.5 g Teflon block, 25.4 mm wide by 41.3 mm long by 19.1 mm thick, with an eye screw fastened in one end was used as a sled. The surface of the sled that contacted to the film was polished using 500-grit sandpaper. The Teflon sled was attached to a flexible beaded chain and pulled using an Instron tensile tester at a rate of 150 mm/min., at 23° C. and 50% R.H. Five measurements was made on each film sample. The thickness of the film was measured using a digital thickness gauge. The kinetic coefficient test results are given in Table I. The maximum kinetic coefficient of friction of five measurements of each film were averaged and reported.

The Differential Scanning Calorimetry (DSC) data were obtained on the following polymers using vacuum dried films in a TA Instruments Model 2920 Modulated DSC in standard (non-modulated) DSC mode. The samples were quenched to −80° C. and heated at 10° C./min to 275° C. in nitrogen. The data are reported as ΔH (J/g) for endothermic, melting events above glass transition temperature (Tg).

TABLE I

Kinetic Coefficient of Polymer Film

| Sample I.D. Wt/wt VDF/HFP | Film Thickness (μm) | Max. Kinetic Coefficient | DSC ΔH (J/g) |
|---|---|---|---|
| Commercial 59.5/40.5 | 22.9 | 2.65 σ = 0.17 | None |
| Polymer 8a 55.1/44.9 | 38.6 | 1.71 σ = 0.09 | 16.5 |
| Polymer 8b 56.8/43.2 | 27.5 | 0.27 σ = 0.03 | 15 |
| Polymer 8c 68.3/31.7 | 25.4 | 0.35 σ = 0.07 | 19.5 |
| Polymer 8d 59.9/40.1 | 21.1 | 2.12 σ = 0.04 | 4.5 |

What is claimed is:

1. An implantable medical device: comprising, a biocompatible film effective to provide an inert surface to be in contact with body tissue of a mammal upon implantation of said device in said mammal, said film comprising a polyfluoro copolymer comprising from about 50 to about 92 weight percent of polymerized residue of vinylidenefluoride and about 50 to about 8 weight percent of polymerized residue of hexafluoropropylene.

2. The device of claim 1, wherein said polyfluoro copolymer comprises from about 50 to about 85 weight percent of said polymerized residue of said vinylidenefluoride copolymerized with from about 50 to about 15 weight percent of said polymerized residue of said hexafluoropropylene.

3. The device of claim 1, wherein said copolymer comprises from about 55 to about 65 weight percent of said polymerized residue of said vinylidenefluoride copolymerized with from about 45 to about 35 weight percent of said polymerized residue of said hexafluoropropylene.

4. The implantable medical device of claim 1, wherein said film further comprises effective amounts of a therapeutic and/or pharmaceutical agent.

5. The implantable device of claim 1 wherein said polyfluoro copolymer is effective to provide said film with properties effective for use in coating said implantable medical device when said coated device is subjected to a maximum temperature of less than 100° C.

* * * * *

(12) EX PARTE REEXAMINATION CERTIFICATE (7607th)
United States Patent
Llanos et al.

(10) Number: US 6,746,773 C1
(45) Certificate Issued: Jul. 13, 2010

(54) COATINGS FOR MEDICAL DEVICES

(75) Inventors: Gerard H. Llanos, Stewartsville, NJ (US); Mark B. Roller, North Brunswick, NJ (US); Angelo Scopelianos, Whitehouse Station, NJ (US); Robert Falotico, Belle Mead, NJ (US)

(73) Assignee: Ethicon, Inc., Somerville, NJ (US)

Reexamination Request:
No. 90/008,372, Mar. 9, 2007

Reexamination Certificate for:
Patent No.: 6,746,773
Issued: Jun. 8, 2004
Appl. No.: 09/962,292
Filed: Sep. 25, 2001

Related U.S. Application Data

(63) Continuation-in-part of application No. 09/675,882, filed on Sep. 29, 2000, now abandoned.

(51) Int. Cl.
| | |
|---|---|
| A61L 17/00 | (2006.01) |
| A61L 17/14 | (2006.01) |
| A61L 27/00 | (2006.01) |
| A61L 27/34 | (2006.01) |
| A61L 29/00 | (2006.01) |
| A61L 29/08 | (2006.01) |
| A61L 31/08 | (2006.01) |
| A61L 31/10 | (2006.01) |
| A61L 31/14 | (2006.01) |
| A61L 31/16 | (2006.01) |
| A61B 17/03 | (2006.01) |
| A61B 17/04 | (2006.01) |
| A61B 17/06 | (2006.01) |
| A61B 17/064 | (2006.01) |
| A61B 17/11 | (2006.01) |
| A61B 17/54 | (2006.01) |
| A61B 17/115 | (2006.01) |
| A61B 17/00 | (2006.01) |
| A61F 2/00 | (2006.01) |
| A61F 2/06 | (2006.01) |

(52) U.S. Cl. ............ 428/421; 604/265; 604/890.1; 604/891.1; 623/1.42; 623/1.43; 623/1.44; 623/1.49

(58) Field of Classification Search .................. None
See application file for complete search history.

(56) References Cited

U.S. PATENT DOCUMENTS

| | | | |
|---|---|---|---|
| 861,659 A | 7/1907 | Johnston | 464/147 |
| 3,051,677 A | 8/1962 | Rexford | |
| 3,279,996 A | 10/1966 | Long et al. | 424/424 |
| 3,526,005 A | 9/1970 | Bokros | 623/11.11 |
| 3,599,641 A | 8/1971 | Sheridan | 604/256 |
| 3,657,744 A | 4/1972 | Ersek | 128/898 |
| 3,744,596 A | 7/1973 | Sander | 188/203 |
| 3,765,414 A | 10/1973 | Arlen | |
| 3,779,805 A | 12/1973 | Alsberg | |
| 3,929,992 A | 12/1975 | Sehgal et al. | 424/122 |
| 3,932,627 A | 1/1976 | Margraf | 514/56 |
| 3,948,254 A | 4/1976 | Zaffaroni | 128/833 |
| 3,952,334 A | 4/1976 | Bokros et al. | 623/11.11 |
| 3,968,800 A | 7/1976 | Vilasi | 606/198 |
| 4,069,307 A | 1/1978 | Higuchi et al. | 424/432 |
| 4,076,285 A | 2/1978 | Martinez | 285/332 |
| 4,252,858 A * | 2/1981 | Chao et al. | 428/421 |
| 4,292,965 A | 10/1981 | Nash et al. | 128/833 |
| 4,299,226 A | 11/1981 | Banka | 604/509 |
| 4,300,244 A | 11/1981 | Bokros | 623/1.13 |
| 4,304,010 A | 12/1981 | Mano | 623/1.46 |
| 4,312,920 A | 1/1982 | Pierce et al. | 428/425.5 |
| 4,321,711 A | 3/1982 | Mano | 623/1.43 |
| 4,323,071 A | 4/1982 | Simpson et al. | 606/194 |
| 4,390,599 A | 6/1983 | Broyles | 428/597 |
| 4,413,359 A | 11/1983 | Akiyama et al. | |
| 4,423,183 A | 12/1983 | Close | |
| 4,441,216 A | 4/1984 | Ionescu et al. | 623/2.19 |
| 4,503,569 A | 3/1985 | Dotter | 623/1.19 |
| 4,512,338 A | 4/1985 | Balko et al. | 606/108 |
| 4,550,447 A | 11/1985 | Seiler, Jr. et al. | 623/1.32 |
| 4,553,545 A | 11/1985 | Maass et al. | 606/198 |
| 4,560,374 A | 12/1985 | Hammerslag | 604/509 |
| 4,562,596 A | 1/1986 | Kronberg | 623/1.32 |
| 4,564,013 A | 1/1986 | Lilenfeld et al. | 606/231 |
| 4,565,740 A | 1/1986 | Golander et al. | 428/409 |
| 4,580,568 A | 4/1986 | Gianturco | 606/198 |
| 4,613,665 A | 9/1986 | Larm | 536/20 |
| 4,642,111 A | 2/1987 | Sakamoto et al. | 424/492 |
| 4,655,771 A | 4/1987 | Wallsten | 623/1.22 |
| 4,656,083 A | 4/1987 | Hoffman et al. | 442/123 |
| 4,676,241 A | 6/1987 | Webb et al. | 128/207.14 |
| 4,678,466 A | 7/1987 | Rosenwald | 424/427 |
| 4,687,482 A | 8/1987 | Hanson | 623/1.49 |
| 4,689,046 A | 8/1987 | Bokros | 623/2.31 |

(Continued)

FOREIGN PATENT DOCUMENTS

| | | |
|---|---|---|
| DE | 3205942 A1 | 9/1983 |
| DE | 19723723 A1 | 12/1998 |
| EP | 0 145 166 A2 | 6/1985 |

(Continued)

OTHER PUBLICATIONS

The American Heritage, Stedman's Medical Dictionary, p. 680, col. 1 and p. 787, col. 1, 1995.*

(Continued)

*Primary Examiner*—Dwayne C Jones

(57) ABSTRACT

The present invention includes biocompatible coatings and films for use on implantable medical devices and medical devices containing such coatings and films applied to a surface thereof, which coatings/films are present on the device in an amount effective to provide an inert surface to be in contact with body tissue of a mammal upon implantation of the device in the mammal, and contain a film-forming polyfluoro copolymer containing the polymerized residue of a moiety selected from the group consisting of vinylidenefluoride and tetrafluoroethylene copolymerized with a second moiety other than the first moiety, wherein the relative amounts of the polymerized residue of the first and second moieties are effective to provide the coating and films with properties effective for use in coating implantable med devices.

U.S. PATENT DOCUMENTS

| | | | |
|---|---|---|---|
| 4,731,054 A | 3/1988 | Billeter et al. | 604/93.01 |
| 4,739,762 A | 4/1988 | Palmaz | 623/1.11 |
| 4,740,207 A | 4/1988 | Kreamer | 623/1.15 |
| 4,753,652 A | 6/1988 | Langer et al. | 623/1.42 |
| 4,760,849 A | 8/1988 | Kropf | 606/191 |
| 4,768,507 A | 9/1988 | Fischell et al. | 623/1.11 |
| 4,776,337 A | 10/1988 | Palmaz | 623/1.11 |
| 4,786,500 A | 11/1988 | Wong | 424/422 |
| 4,787,899 A | 11/1988 | Lazarus | 623/1.11 |
| 4,800,882 A | 1/1989 | Gianturco | |
| 4,810,784 A | 3/1989 | Larm | 536/20 |
| 4,856,516 A | 8/1989 | Hillstead | 606/194 |
| 4,871,357 A | 10/1989 | Hsu et al. | |
| 4,872,867 A | 10/1989 | Joh | 604/269 |
| 4,876,109 A | 10/1989 | Mayer et al. | |
| 4,886,062 A * | 12/1989 | Wiktor | 606/194 |
| 4,907,336 A | 3/1990 | Gianturco | 29/515 |
| 4,916,193 A | 4/1990 | Tang et al. | 525/413 |
| 4,950,256 A | 8/1990 | Luther et al. | |
| 4,954,126 A | 9/1990 | Wallsten | 600/36 |
| 4,969,458 A | 11/1990 | Wiktor | 623/1.11 |
| 4,990,131 A | 2/1991 | Dardik et al. | 600/36 |
| 4,990,155 A | 2/1991 | Wilkoff | 606/191 |
| 4,994,071 A | 2/1991 | MacGregor | 606/194 |
| 4,994,298 A | 2/1991 | Yasuda | 427/490 |
| 4,998,923 A | 3/1991 | Samson et al. | 606/194 |
| 5,015,253 A | 5/1991 | MacGregor | 623/1.15 |
| 5,019,090 A | 5/1991 | Pinchuk | 623/1.15 |
| 5,019,096 A | 5/1991 | Fox, Jr. et al. | 600/36 |
| 5,029,877 A | 7/1991 | Fedeli | 277/354 |
| 5,034,265 A | 7/1991 | Hoffman et al. | 442/126 |
| 5,035,706 A | 7/1991 | Gianturco et al. | 606/198 |
| 5,041,100 A | 8/1991 | Rowland et al. | 604/265 |
| 5,041,126 A | 8/1991 | Gianturco | 623/1.15 |
| 5,047,020 A | 9/1991 | Hsu | |
| 5,049,132 A | 9/1991 | Shaffer et al. | 604/101.02 |
| 5,049,403 A | 9/1991 | Larm et al. | 427/2.1 |
| 5,053,048 A | 10/1991 | Pinchuk | |
| 5,059,166 A | 10/1991 | Fischell et al. | 600/3 |
| 5,061,275 A | 10/1991 | Wallsten et al. | 623/1.22 |
| 5,061,276 A | 10/1991 | Tu et al. | 623/1.33 |
| 5,061,750 A | 10/1991 | Feijen et al. | 525/54.1 |
| 5,064,435 A | 11/1991 | Porter | 623/23.7 |
| 5,092,877 A | 3/1992 | Pinchuk | 128/898 |
| 5,102,417 A | 4/1992 | Palmaz | 606/195 |
| 5,104,404 A | 4/1992 | Wolff | 623/1.16 |
| 5,116,365 A | 5/1992 | Hillstead | 623/1.15 |
| 5,122,154 A | 6/1992 | Rhodes | 623/1.13 |
| 5,131,908 A | 7/1992 | Dardik et al. | 600/36 |
| 5,133,732 A | 7/1992 | Wiktor | 623/1.22 |
| 5,134,192 A | 7/1992 | Feijen et al. | 525/54.1 |
| 5,135,536 A | 8/1992 | Hillstead | 606/195 |
| 5,163,952 A | 11/1992 | Froix | 623/1.18 |
| 5,163,958 A | 11/1992 | Pinchuk | 623/23.49 |
| 5,171,217 A | 12/1992 | March et al. | 604/507 |
| 5,171,262 A | 12/1992 | MacGregor | 623/1.15 |
| 5,176,660 A | 1/1993 | Truckai | 604/527 |
| 5,176,972 A | 1/1993 | Bloom et al. | |
| 5,178,618 A | 1/1993 | Kandarpa | 606/28 |
| 5,180,366 A | 1/1993 | Woods | 604/96.01 |
| 5,182,317 A | 1/1993 | Winters et al. | 523/112 |
| 5,185,408 A | 2/1993 | Tang et al. | |
| 5,192,307 A | 3/1993 | Wall | 623/1.2 |
| 5,195,984 A | 3/1993 | Schalz | 623/1.2 |
| 5,199,951 A | 4/1993 | Spears | |
| 5,202,332 A | 4/1993 | Hughes et al. | |
| 5,213,576 A | 5/1993 | Abiuso et al. | 604/103.01 |
| 5,213,898 A | 5/1993 | Larm et al. | 428/422 |
| 5,217,483 A | 6/1993 | Tower | 623/1.15 |
| 5,222,971 A | 6/1993 | Willard et al. | 606/198 |
| 5,226,913 A | 7/1993 | Pinchuk | 140/71 R |
| 5,234,456 A | 8/1993 | Silvestrini | 623/1.2 |
| 5,246,445 A | 9/1993 | Yachia et al. | 623/1.2 |
| 5,252,579 A | 10/1993 | Skotnicki et al. | |
| 5,256,790 A | 10/1993 | Nelson | |
| 5,258,020 A | 11/1993 | Froix | 128/898 |
| 5,258,021 A | 11/1993 | Duran | 623/2.3 |
| 5,262,451 A | 11/1993 | Winters et al. | 523/112 |
| 5,266,073 A | 11/1993 | Wall | 623/1.2 |
| 5,272,012 A | 12/1993 | Opolski | 428/423.1 |
| 4,733,665 A | 1/1994 | Palmaz | 606/108 |
| 5,275,622 A | 1/1994 | Lazarus et al. | 623/1.11 |
| 5,282,823 A | 2/1994 | Schwartz et al. | 623/1.22 |
| 5,282,824 A | 2/1994 | Gianturco | 623/1.13 |
| 5,283,257 A | 2/1994 | Gregory et al. | 514/458 |
| 5,288,711 A | 2/1994 | Mitchell et al. | 424/122 |
| 5,290,305 A | 3/1994 | Inoue | 623/1.2 |
| 5,292,331 A | 3/1994 | Boneau | 623/1.16 |
| 5,292,802 A | 3/1994 | Rhee et al. | 525/54.1 |
| 5,304,121 A | 4/1994 | Sahatjian | 604/509 |
| 5,304,200 A | 4/1994 | Spaulding | 623/1.16 |
| 5,306,250 A | 4/1994 | March et al. | 604/104 |
| 5,308,862 A | 5/1994 | Ohlstein | 514/411 |
| 5,308,889 A | 5/1994 | Rhee et al. | 523/113 |
| 5,311,884 A | 5/1994 | Scopelianos | 128/858 |
| 5,314,444 A | 5/1994 | Gianturco | 606/195 |
| 5,314,472 A | 5/1994 | Fontaine | 623/1.22 |
| 5,328,471 A | 7/1994 | Slepian | 604/101.03 |
| 5,334,301 A | 8/1994 | Heinke et al. | 204/267 |
| 5,336,518 A | 8/1994 | Narayanan et al. | |
| 5,338,770 A | 8/1994 | Winters et al. | 523/112 |
| 5,342,348 A | 8/1994 | Kaplan | |
| 5,342,387 A | 8/1994 | Summers | 606/198 |
| 5,342,621 A | 8/1994 | Eury | 606/198 |
| 5,354,257 A | 10/1994 | Roubin et al. | 600/7 |
| 5,354,308 A | 10/1994 | Simon et al. | 623/1.15 |
| 5,356,433 A | 10/1994 | Rowland et al. | 424/422 |
| 5,362,718 A | 11/1994 | Skotnicki et al. | |
| 5,366,504 A | 11/1994 | Andersen et al. | 623/1.5 |
| 5,368,566 A | 12/1994 | Crocker | |
| 5,370,683 A | 12/1994 | Fontaine | 623/1.22 |
| 5,370,691 A | 12/1994 | Samson | 623/1.22 |
| 5,375,612 A | 12/1994 | Cottenceau et al. | 128/899 |
| 5,376,112 A | 12/1994 | Duran | 623/1.26 |
| 5,378,475 A | 1/1995 | Smith et al. | 424/473 |
| 5,378,836 A | 1/1995 | Kao et al. | |
| 5,380,299 A | 1/1995 | Fearnot et al. | |
| 5,382,261 A | 1/1995 | Palmaz | 606/158 |
| 5,383,853 A | 1/1995 | Jung et al. | 604/103.04 |
| 5,383,928 A | 1/1995 | Scott et al. | |
| 5,385,908 A | 1/1995 | Nelson et al. | |
| 5,385,909 A | 1/1995 | Nelson et al. | |
| 5,385,910 A | 1/1995 | Ocain et al. | |
| 5,387,235 A | 2/1995 | Chuter | 623/1.11 |
| 5,387,680 A | 2/1995 | Nelson | |
| 5,389,106 A | 2/1995 | Tower | 623/1.15 |
| 5,389,639 A | 2/1995 | Failli et al. | |
| 5,391,730 A | 2/1995 | Skotnicki et al. | |
| 5,393,772 A | 2/1995 | Yue et al. | 514/410 |
| 5,395,390 A | 3/1995 | Simon et al. | 623/1.18 |
| 5,397,355 A | 3/1995 | Marin et al. | 623/1.2 |
| 5,399,352 A | 3/1995 | Hanson | 424/423 |
| 5,403,341 A | 4/1995 | Solar | |
| 5,405,377 A | 4/1995 | Cragg | 623/1.2 |
| 5,409,696 A | 4/1995 | Narayanan et al. | 424/78.17 |
| 5,411,549 A | 5/1995 | Peters | 623/1.15 |
| 5,415,619 A | 5/1995 | Lee et al. | 600/36 |
| 5,417,969 A | 5/1995 | Hsu et al. | |
| 5,419,760 A | 5/1995 | Narciso, Jr. | 604/8 |
| D359,802 S | 6/1995 | Fontaine | D24/155 |
| 5,421,955 A | 6/1995 | Lau et al. | 216/48 |

| | | | | | | |
|---|---|---|---|---|---|---|
| 5,423,885 A | 6/1995 | Williams .................. 623/1.17 | 5,620,984 A | 4/1997 | Bianco et al. .......... 514/263.36 |
| 5,429,618 A | 7/1995 | Keogh ........................ 604/266 | 5,621,102 A | 4/1997 | Bianco et al. ............... 544/267 |
| 5,429,634 A | 7/1995 | Narciso, Jr. .............. 604/890.1 | 5,622,975 A | 4/1997 | Singh et al. ................. 514/324 |
| 5,439,446 A | 8/1995 | Barry .................... 604/103.01 | 5,624,411 A | 4/1997 | Tuch .......................... 604/265 |
| 5,441,515 A | 8/1995 | Khosravi et al. ............. 606/194 | 5,628,785 A | 5/1997 | Schwartz et al. ............ 128/898 |
| 5,441,516 A | 8/1995 | Wang et al. .................. 606/198 | 5,628,786 A | 5/1997 | Banas et al. ................ 623/1.13 |
| 5,441,947 A | 8/1995 | Dodge et al. ................. 514/179 | 5,629,077 A | 5/1997 | Turnlund et al. ............ 623/1.15 |
| 5,441,977 A | 8/1995 | Russo et al. | 5,629,315 A | 5/1997 | Bianco et al. .......... 514/263.36 |
| 5,443,458 A | 8/1995 | Eury | 5,632,763 A | 5/1997 | Glastra ....................... 623/1.15 |
| 5,443,477 A | 8/1995 | Marin et al. ................. 606/198 | 5,632,771 A | 5/1997 | Boatman et al. |
| 5,443,496 A | 8/1995 | Schwartz et al. ........... 623/1.16 | 5,632,776 A | 5/1997 | Kurumatani et al. |
| 5,443,498 A | 8/1995 | Fontaine ................... 623/1.17 | 5,632,840 A | 5/1997 | Campbell |
| 5,443,500 A | 8/1995 | Sigwart ...................... 623/1.17 | 5,635,201 A | 6/1997 | Fabo |
| 5,447,724 A | 9/1995 | Helmus et al. | 5,637,113 A | 6/1997 | Tartaglia et al. ............. 623/1.42 |
| 5,449,372 A | 9/1995 | Schmaltz et al. ............ 606/198 | 5,643,312 A | 7/1997 | Fischell et al. ............. 623/1.15 |
| 5,449,373 A | 9/1995 | Pinchasik et al. ........... 606/198 | 5,643,939 A | 7/1997 | Ohlstein ..................... 514/411 |
| 5,449,382 A | 9/1995 | Dayton ....................... 623/1.15 | 5,646,160 A | 7/1997 | Morris et al. ................ 514/291 |
| 5,464,450 A | 11/1995 | Buscemi et al. ............... 632/1.2 | 5,648,357 A | 7/1997 | Bianco et al. ........ 514/263.36 |
| 5,464,540 A | 11/1995 | Friesen et al. ............... 210/640 | 5,649,952 A | 7/1997 | Lam .......................... 623/1.15 |
| 5,464,650 A | 11/1995 | Berg et al. | 5,649,977 A | 7/1997 | Campbell ................... 623/1.15 |
| 5,472,985 A | 12/1995 | Grainger et al. | 5,651,174 A | 7/1997 | Schwartz et al. ........... 29/527.2 |
| 5,474,563 A | 12/1995 | Myler et al. ................. 606/108 | 5,652,243 A | 7/1997 | Bianco et al. .......... 514/263.36 |
| 5,486,357 A | 1/1996 | Narayanan ............... 424/78.17 | 5,653,747 A | 8/1997 | Dereume ..................... 623/1.54 |
| 5,491,231 A | 2/1996 | Nelson et al. | 5,653,992 A | 8/1997 | Bezwada et al. ............ 424/426 |
| 5,496,365 A | 3/1996 | Sgro ............................ 623/1.2 | 5,660,873 A | 8/1997 | Nikolaychik et al. |
| 5,500,013 A | 3/1996 | Buscemi et al. ............ 623/1.22 | 5,662,609 A | 9/1997 | Slepian ................... 604/101.03 |
| 5,504,091 A | 4/1996 | Molnar-Kimber et al. | 5,665,591 A | 9/1997 | Sonenshein et al. ......... 435/375 |
| 5,508,286 A | 4/1996 | Skotnicki et al. | 5,665,728 A | 9/1997 | Morris et al. |
| 5,510,077 A | 4/1996 | Dinh et al. ................... 264/485 | 5,665,772 A | 9/1997 | Cottens et al. |
| 5,512,055 A | 4/1996 | Domb et al. ................. 604/265 | 5,667,764 A | 9/1997 | Kopia et al. ................ 424/1.45 |
| 5,514,680 A | 5/1996 | Weber et al. | 5,669,924 A | 9/1997 | Shaknovich ................ 623/1.11 |
| 5,516,781 A | 5/1996 | Morris et al. ................ 514/291 | 5,670,506 A | 9/1997 | Leigh et al. ................. 514/141 |
| 5,519,042 A | 5/1996 | Morris et al. ................ 514/378 | 5,672,638 A | 9/1997 | Verhoeven et al. .......... 523/112 |
| 5,523,092 A | 6/1996 | Hanson et al. ............... 424/423 | 5,674,242 A | 10/1997 | Phan et al. ................... 606/198 |
| 5,525,610 A | 6/1996 | Caufield et al. | 5,679,400 A | 10/1997 | Tuch |
| 5,527,354 A | 6/1996 | Fontaine et al. ............ 623/1.17 | 5,679,659 A | 10/1997 | Verhoeven et al. ............ 514/56 |
| 5,541,191 A | 7/1996 | Skotnicki et al. | 5,684,061 A | 11/1997 | Ohnishi et al. |
| 5,545,208 A | 8/1996 | Wolff et al. | 5,691,311 A | 11/1997 | Marqganore et al. |
| 5,551,954 A | 9/1996 | Buscemi et al. ............ 623/1.15 | 5,693,085 A | 12/1997 | Buirge et al. ............... 623/1.13 |
| 5,554,182 A | 9/1996 | Dinh et al. ..................... 600/36 | 5,697,967 A | 12/1997 | Dinh et al. |
| 5,554,954 A | 9/1996 | Takahashi .................... 327/546 | 5,697,971 A | 12/1997 | Fischell et al. ............. 623/1.15 |
| 5,556,413 A | 9/1996 | Lam ............................ 623/1.2 | 5,700,286 A | 12/1997 | Tartaglia et al. ............. 623/1.15 |
| 5,559,122 A | 9/1996 | Nelson et al. | 5,707,385 A | 1/1998 | Williams .................... 606/192 |
| 5,562,922 A | 10/1996 | Lambert ...................... 424/486 | 5,709,874 A | 1/1998 | Hanson et al. ............... 424/423 |
| 5,563,145 A | 10/1996 | Failli et al. | 5,710,174 A | 1/1998 | West et al. |
| 5,563,146 A | 10/1996 | Morris ........................ 514/291 | 5,713,949 A | 2/1998 | Jayaraman |
| 5,569,197 A | 10/1996 | Helmus ................... 604/102.02 | 5,716,981 A | 2/1998 | Hunter et al. |
| 5,569,295 A | 10/1996 | Lam ............................ 606/198 | 5,725,549 A | 3/1998 | Lam .......................... 623/1.15 |
| 5,569,462 A | 10/1996 | Martinson et al. ........... 424/423 | 5,725,567 A | 3/1998 | Wolff et al. ................. 623/1.42 |
| 5,569,463 A | 10/1996 | Helmus et al. | 5,728,150 A | 3/1998 | McDonald et al. ......... 623/1.15 |
| 5,571,089 A | 11/1996 | Crocker ................. 604/103.01 | 5,728,420 A | 3/1998 | Keogh ....................... 427/2.12 |
| 5,571,166 A | 11/1996 | Dinh et al. ................... 128/898 | 5,731,326 A | 3/1998 | Hart et al. .................... 514/323 |
| 5,574,059 A | 11/1996 | Regunathan et al. ........ 514/397 | 5,733,327 A | 3/1998 | Igaki et al. ................... 623/1.5 |
| 5,575,818 A | 11/1996 | Pinchuk | 5,733,920 A | 3/1998 | Mansuri et al. .............. 514/337 |
| 5,578,075 A | 11/1996 | Dayton ....................... 623/1.15 | 5,733,925 A | 3/1998 | Kunz et al. .................. 514/449 |
| 5,580,873 A | 12/1996 | Bianco et al. .......... 514/263.36 | 5,735,897 A | 4/1998 | Buirge ....................... 623/1.15 |
| 5,580,874 A | 12/1996 | Bianco et al. .......... 514/263.36 | 5,739,138 A | 4/1998 | Bianco et al. .......... 514/263.36 |
| 5,591,140 A | 1/1997 | Narayanan et al. .......... 604/269 | 5,744,587 A | 4/1998 | Alaska et al. |
| 5,591,197 A | 1/1997 | Orth et al. .................. 623/1.16 | 5,755,734 A | 5/1998 | Richter et al. ............... 606/194 |
| 5,591,224 A | 1/1997 | Schwartz et al. | 5,755,772 A | 5/1998 | Evans et al. ................. 128/898 |
| 5,591,227 A | 1/1997 | Dinh et al. .................. 623/1.22 | 5,759,205 A | 6/1998 | Valentini |
| 5,599,352 A | 2/1997 | Dinh et al. ................... 128/898 | 5,769,883 A | 6/1998 | Buscemi et al. ............ 623/1.42 |
| 5,599,844 A | 2/1997 | Grainger et al. | 5,776,184 A | 7/1998 | Tuch |
| 5,603,722 A | 2/1997 | Phan et al. ................. 623/1.18 | 5,780,462 A | 7/1998 | Lee et al. |
| 5,604,283 A | 2/1997 | Wada et al. | 5,780,476 A | 7/1998 | Underiner et al. ....... 514/263.36 |
| 5,605,696 A | 2/1997 | Eury et al. ................... 424/423 | 5,782,908 A | 7/1998 | Cahalan et al. ............. 623/1.13 |
| 5,607,463 A | 3/1997 | Schwartz et al. ........... 623/1.44 | 5,786,171 A | 7/1998 | Lee et al. |
| 5,607,475 A | 3/1997 | Cahalan et al. ............. 424/423 | 5,788,979 A | 8/1998 | Alt et al. ..................... 424/426 |
| 5,609,629 A | 3/1997 | Fearnot et al. .............. 623/1.42 | 5,792,106 A | 8/1998 | Mische .................. 604/103.01 |
| 5,616,608 A | 4/1997 | Kinsella et al. | 5,792,772 A | 8/1998 | Bianco et al. .......... 514/263.36 |
| 5,618,837 A | 4/1997 | Hart et al. | 5,798,372 A | 8/1998 | Davies et al. ............... 514/356 |

| Patent No. | Date | Inventor | Class |
|---|---|---|---|
| 5,799,384 A | 9/1998 | Schwartz et al. | 29/458 |
| 5,800,507 A | 9/1998 | Schwartz | 623/1.11 |
| 5,800,508 A | 9/1998 | Goicoechea et al. | 623/1.15 |
| 5,807,743 A | 9/1998 | Stinchcomb et al. | |
| 5,807,861 A | 9/1998 | Klein et al. | 514/263.35 |
| 5,811,447 A | 9/1998 | Kunz et al. | 514/411 |
| 5,820,917 A | 10/1998 | Tuch | 427/2.1 |
| 5,820,918 A | 10/1998 | Ronan et al. | 427/2.1 |
| 5,824,048 A | 10/1998 | Tuch | |
| 5,824,049 A | 10/1998 | Ragheb et al. | |
| 5,827,587 A | 10/1998 | Fukushi | |
| 5,827,734 A | 10/1998 | Weigle et al. | |
| 5,833,651 A | 11/1998 | Donovan et al. | 604/509 |
| 5,837,008 A | 11/1998 | Berg et al. | 128/898 |
| 5,837,313 A | 11/1998 | Ding et al. | 427/2.21 |
| 5,843,120 A | 12/1998 | Israel et al. | 623/1.15 |
| 5,843,166 A | 12/1998 | Lentz et al. | 623/1.13 |
| 5,843,172 A | 12/1998 | Yan | 623/1.42 |
| 5,849,034 A | 12/1998 | Schwartz | 606/36 |
| 5,851,217 A | 12/1998 | Wolff et al. | 606/191 |
| 5,851,231 A | 12/1998 | Wolff et al. | 623/1.42 |
| 5,858,967 A | 1/1999 | Weigle et al. | |
| 5,858,990 A | 1/1999 | Walsh | 514/44 |
| 5,861,027 A | 1/1999 | Trapp | 623/1.15 |
| 5,865,814 A | 2/1999 | Tuch | |
| 5,871,535 A | 2/1999 | Wolff et al. | 128/898 |
| 5,873,904 A | 2/1999 | Ragheb et al. | |
| 5,876,433 A | 3/1999 | Lunn | 623/1.15 |
| 5,877,224 A | 3/1999 | Brocchini et al. | 514/772.2 |
| 5,879,697 A | 3/1999 | Ding et al. | |
| 5,882,335 A | 3/1999 | Leone et al. | 604/103.02 |
| 5,883,110 A | 3/1999 | Tang et al. | |
| 5,891,108 A | 4/1999 | Leone et al. | 604/264 |
| 5,893,840 A | 4/1999 | Hull et al. | 604/103.02 |
| 5,897,911 A | 4/1999 | Loeffler | |
| 5,900,246 A | 5/1999 | Lambert | 424/429 |
| 5,902,266 A | 5/1999 | Leone et al. | 604/509 |
| 5,912,253 A | 6/1999 | Cottens et al. | |
| 5,916,910 A | 6/1999 | Lai | 514/423 |
| 5,922,393 A | 7/1999 | Jayaraman | |
| 5,922,730 A | 7/1999 | Hu et al. | |
| 5,932,243 A | 8/1999 | Fricker et al. | 424/450 |
| 5,932,299 A | 8/1999 | Katoot | |
| 5,932,580 A | 8/1999 | Levitzki et al. | 181/152 |
| 5,951,586 A | 9/1999 | Berg et al. | 606/198 |
| 5,957,971 A | 9/1999 | Schwartz | 623/1.15 |
| 5,959,075 A | 9/1999 | Lok et al. | |
| 5,962,265 A | 10/1999 | Norris et al. | |
| 5,968,091 A | 10/1999 | Pinchuk et al. | 623/1.16 |
| 5,972,027 A | 10/1999 | Johnson | 623/1.42 |
| 5,976,534 A | 11/1999 | Hart et al. | 424/145.1 |
| 5,977,163 A | 11/1999 | Li et al. | 514/449 |
| 5,980,553 A | 11/1999 | Gray et al. | 623/1.15 |
| 5,980,566 A | 11/1999 | Alt et al. | 623/23.7 |
| 5,980,972 A | 11/1999 | Ding | 427/2.24 |
| 5,981,568 A | 11/1999 | Kunz et al. | 514/411 |
| 5,985,307 A | 11/1999 | Hanson et al. | 424/423 |
| 5,986,049 A | 11/1999 | Forstrom et al. | |
| 5,997,468 A | 12/1999 | Wolff et al. | 606/36 |
| 6,004,346 A | 12/1999 | Wolff et al. | 623/23.71 |
| 6,015,432 A | 1/2000 | Rakos et al. | 623/1.13 |
| 6,015,815 A | 1/2000 | Mollison | |
| 6,039,721 A | 3/2000 | Johnson et al. | 604/508 |
| 6,059,813 A | 5/2000 | Vrba et al. | 606/198 |
| 6,071,305 A | 6/2000 | Brown et al. | 623/1.43 |
| 6,074,659 A | 6/2000 | Kunz et al. | 424/423 |
| 6,080,190 A | 6/2000 | Schwartz et al. | 623/1.22 |
| 6,096,070 A | 8/2000 | Ragheb et al. | 623/1.39 |
| 6,099,562 A | 8/2000 | Ding et al. | 623/1.46 |
| 6,120,536 A | 9/2000 | Ding et al. | 623/1.43 |
| 6,120,847 A | 9/2000 | Yang et al. | 427/335 |
| 6,136,798 A | 10/2000 | Cody et al. | 514/141 |
| 6,140,127 A | 10/2000 | Sprague | 435/395 |
| 6,146,358 A | 11/2000 | Rowe | 604/103 |
| 6,153,252 A | 11/2000 | Hossainy et al. | |
| 6,159,488 A | 12/2000 | Nagier et al. | 424/423 |
| 6,171,232 B1 | 1/2001 | Papandreou et al. | 600/36 |
| 6,171,609 B1 | 1/2001 | Kunz | 424/422 |
| 6,177,272 B1 | 1/2001 | Nabel et al. | 435/320.1 |
| 6,179,817 B1 | 1/2001 | Zhong | 604/265 |
| 6,187,757 B1 | 2/2001 | Clackson et al. | |
| 6,193,746 B1 | 2/2001 | Strecker | 623/1.13 |
| 6,214,901 B1 | 4/2001 | Chudzik et al. | 523/113 |
| 6,225,346 B1 | 5/2001 | Tang et al. | 514/523 |
| 6,240,616 B1 | 6/2001 | Yan | 29/527.2 |
| 6,245,537 B1 | 6/2001 | Williams et al. | 435/135 |
| 6,251,920 B1 | 6/2001 | Grainger et al. | 514/319 |
| 6,254,632 B1 | 7/2001 | Wu et al. | 623/1.15 |
| 6,254,634 B1 | 7/2001 | Anderson et al. | 623/1.42 |
| 6,258,121 B1 | 7/2001 | Yang et al. | 623/1.46 |
| 6,268,390 B1 | 7/2001 | Kunz | 514/411 |
| 6,273,913 B1 | 8/2001 | Wright et al. | 623/1.42 |
| 6,284,305 B1 | 9/2001 | Ding et al. | 427/2.28 |
| 6,287,320 B1 | 9/2001 | Slepian | 606/194 |
| 6,287,628 B1 | 9/2001 | Hossainy et al. | 427/2.3 |
| 6,299,604 B1 | 10/2001 | Ragheb et al. | 604/265 |
| 6,306,144 B1 | 10/2001 | Sydney et al. | 606/108 |
| 6,306,166 B1 | 10/2001 | Barry et al. | 623/1.46 |
| 6,306,176 B1 | 10/2001 | Whitbourne | 623/23.59 |
| 6,306,421 B1 | 10/2001 | Kunz et al. | 424/423 |
| 6,309,380 B1 | 10/2001 | Larson et al. | 604/502 |
| 6,309,660 B1 | 10/2001 | Hsu et al. | 424/425 |
| 6,313,264 B1 | 11/2001 | Caggiano et al. | 530/350 |
| 6,316,018 B1 | 11/2001 | Ding et al. | 424/423 |
| 6,335,029 B1 | 1/2002 | Kamath et al. | 424/423 |
| 6,358,556 B1 | 3/2002 | Ding et al. | 427/2.24 |
| 6,368,658 B1 | 4/2002 | Schartz et al. | |
| 6,369,039 B1 | 4/2002 | Palasis et al. | 424/93.2 |
| 6,379,382 B1 | 4/2002 | Yang | 623/1.42 |
| 6,384,046 B1 | 5/2002 | Schuler et al. | |
| 6,387,121 B1 | 5/2002 | Alt | 623/1.15 |
| 6,403,635 B1 | 6/2002 | Kinsella et al. | 514/449 |
| 6,407,067 B1 | 6/2002 | Schafer | 514/19 |
| 6,448,221 B1 | 9/2002 | Sheppard et al. | |
| 6,471,979 B2 | 10/2002 | New et al. | |
| 6,471,980 B2 | 10/2002 | Sirhan et al. | |
| 6,517,858 B1 | 2/2003 | Le Moel et al. | 424/424 |
| 6,517,889 B1 | 2/2003 | Jayaraman | 427/2.24 |
| 6,545,097 B2 | 4/2003 | Pinchuk et al. | 525/240 |
| 6,585,764 B2 | 7/2003 | Wright et al. | 623/1.42 |
| 6,620,194 B2 | 9/2003 | Ding et al. | 623/1.43 |
| 6,623,521 B2 | 9/2003 | Steinke et al. | |
| 6,627,246 B2 | 9/2003 | Mehta et al. | |
| 6,663,606 B1 | 12/2003 | Barry et al. | 606/264 |
| 6,673,385 B1 | 1/2004 | Ding et al. | |
| 6,746,773 B2 | 6/2004 | Llanos et al. | 428/421 |
| 6,776,796 B2 | 8/2004 | Falotico et al. | 623/1.46 |
| 6,808,536 B2 | 10/2004 | Wright et al. | 623/1.42 |
| 6,818,247 B1 | 11/2004 | Chen et al. | |
| 6,833,153 B1 | 12/2004 | Roorda et al. | 427/2.24 |
| 6,872,225 B1 | 3/2005 | Rowan et al. | |
| 6,939,375 B2 | 9/2005 | Sirhan et al. | |
| 7,018,405 B2 | 3/2006 | Sirhan et al. | |
| 7,048,939 B2 | 5/2006 | Elkins et al. | |
| 7,056,339 B2 | 6/2006 | Elkins et al. | |
| 7,087,078 B2 | 8/2006 | Hildebrand et al. | |
| 7,135,039 B2 | 11/2006 | De Scheerder et al. | |
| 7,186,518 B2 | 3/2007 | Wang et al. | |
| 7,223,286 B2 | 5/2007 | Wright et al. | |
| 7,300,662 B2 | 11/2007 | Falotico et al. | |
| 2001/0007083 A1 | 7/2001 | Roorda | 623/1.15 |
| 2001/0029351 A1 | 10/2001 | Falotico et al. | 604/103.02 |

| | | | |
|---|---|---|---|
| 2001/0029660 A1 | 10/2001 | Johnson .................. 29/557 |
| 2001/0032014 A1 | 10/2001 | Yang et al. ............. 623/1.15 |
| 2001/0034363 A1 | 10/2001 | Li et al. ................. 514/449 |
| 2001/0037145 A1 | 11/2001 | Guruwaiya et al. ....... 623/1.15 |
| 2002/0010418 A1 | 1/2002 | Lary et al. ............. 604/101.04 |
| 2002/0032477 A1 | 3/2002 | Helmus et al. .......... 623/1.2 |
| 2002/0041899 A1 | 4/2002 | Chudzik et al. ......... 424/487 |
| 2002/0061326 A1 | 5/2002 | Li et al. ................ 424/424 |
| 2002/0068969 A1 | 6/2002 | Shanley et al. ......... 623/1.16 |
| 2002/0071902 A1 | 6/2002 | Ding et al. ............. 427/2.24 |
| 2002/0082680 A1 | 6/2002 | Shanley et al. ......... 623/1.16 |
| 2002/0082685 A1 | 6/2002 | Sirhan et al. .......... 623/1.42 |
| 2002/0091433 A1 | 7/2002 | Ding et al. ............. 623/1.2 |
| 2002/0095114 A1 | 7/2002 | Palasis ................ 604/96.01 |
| 2002/0099438 A1 | 7/2002 | Furst .................. 623/1.16 |
| 2002/0103526 A1 | 8/2002 | Steinke ................ 623/1.11 |
| 2002/0119178 A1 | 8/2002 | Levesque et al. ....... 424/423 |
| 2002/0123505 A1 | 9/2002 | Mollison et al. ........ 514/291 |
| 2002/0127377 A1 | 9/2002 | Schwartz et al. ........ 427/2.15 |
| 2002/0133222 A1 | 9/2002 | Das ..................... 623/1.16 |
| 2002/0133224 A1 | 9/2002 | Bajgar et al. ........... 623/1.39 |
| 2002/0165608 A1 | 11/2002 | Llanos ................. 604/500 |
| 2002/0193475 A1 | 12/2002 | Hossainy et al. ........ 524/113 |
| 2003/0065377 A1 | 4/2003 | Davila et al. .......... 604/265 |
| 2003/0216699 A1 | 11/2003 | Falotico ............... 604/265 |
| 2004/0049265 A1 | 3/2004 | Ding et al. ............ 623/1.42 |
| 2004/0243097 A1 | 12/2004 | Falotico et al. ........ 604/500 |
| 2004/0260268 A1 | 12/2004 | Falotico et al. ........ 604/500 |
| 2005/0002986 A1 | 1/2005 | Falotico et al. ........ 424/426 |
| 2005/0004663 A1 | 1/2005 | Llanos et al. .......... 623/1.46 |
| 2005/0033261 A1 | 2/2005 | Falotico et al. ........ 604/500 |
| 2005/0106210 A1 | 5/2005 | Ding et al. ............ 424/423 |
| 2005/0187611 A1 | 8/2005 | Ding et al. ............ 623/1.15 |
| 2005/0208200 A1 | 9/2005 | Ding et al. ............ 427/2.25 |
| 2006/0088654 A1 | 4/2006 | Ding et al. ............ 427/2.21 |
| 2006/0089705 A1 | 4/2006 | Ding et al. ............ 623/1.15 |
| 2006/0222756 A1 | 10/2006 | Davila et al. .......... 427/2.24 |
| 2006/0235503 A1 | 10/2006 | Llanos et al. |
| 2007/0276473 A1 | 11/2007 | Llanos et al. |
| 2007/0276474 A1 | 11/2007 | Llanos et al. |
| 2007/0276475 A1 | 11/2007 | Llanos et al. |
| 2007/0276476 A1 | 11/2007 | Llanos et al. |

FOREIGN PATENT DOCUMENTS

| | | |
|---|---|---|
| EP | 0 177 330 A2 | 4/1986 |
| EP | 0 183 372 A1 | 6/1986 |
| EP | 0 221 570 A2 | 5/1987 |
| EP | 0 421 729 A2 | 4/1991 |
| EP | 0 540 290 A2 | 5/1993 |
| EP | 0 551 182 A1 | 7/1993 |
| EP | 0 568 310 A1 | 11/1993 |
| EP | 0 604 022 A1 | 6/1994 |
| EP | 0 621 015 A1 | 10/1994 |
| EP | 0 623 354 A1 | 11/1994 |
| EP | 0 734 698 A2 | 3/1996 |
| EP | 0 712 615 A1 | 5/1996 |
| EP | 0 716 836 A1 | 6/1996 |
| EP | 0 734 721 A2 | 10/1996 |
| EP | 0 747 069 A3 | 12/1996 |
| EP | 0 747 069 A2 | 12/1996 |
| EP | 0 761 251 A1 | 3/1997 |
| EP | 0 800 801 A1 | 10/1997 |
| EP | 0 540 290 B1 | 1/1998 |
| EP | 0 830 853 A1 | 3/1998 |
| EP | 0 815 803 A1 | 7/1998 |
| EP | 0 850 651 A2 | 7/1998 |
| EP | 0 938 878 A2 | 9/1999 |
| EP | 0 938 878 A3 | 9/1999 |
| EP | 0 950 386 A2 | 10/1999 |
| EP | 0 968 688 A1 | 1/2000 |
| EP | 0 970 711 A2 | 1/2000 |
| EP | 0 950 386 A3 | 4/2000 |
| EP | 0 551 182 B1 | 7/2000 |
| EP | 0 970 711 A3 | 1/2001 |
| EP | 0 633 032 B1 | 2/2001 |
| EP | 1 192 957 A2 | 4/2002 |
| EP | 0 747 069 B1 | 9/2002 |
| EP | 0 950 386 B1 | 4/2004 |
| EP | 0 970 711 B1 | 10/2004 |
| EP | 1 588 726 A1 | 10/2005 |
| EP | 1 588 727 A1 | 10/2005 |
| FR | 2 785 812 | 5/2000 |
| GB | 0 662 307 A2 | 12/1951 |
| GB | 789786 | 1/1958 |
| GB | 1001765 | 8/1965 |
| GB | 1 205 743 A | 9/1970 |
| GB | 2 135 585 A | 9/1984 |
| WO | 89/03232 A1 | 4/1989 |
| WO | 91/12779 A1 | 9/1991 |
| WO | WO 91/17724 A1 | 11/1991 |
| WO | 92/15286 A1 | 9/1992 |
| WO | 94/01056 A1 | 1/1994 |
| WO | 94/21308 A1 | 9/1994 |
| WO | 94/21309 A1 | 9/1994 |
| WO | 94/24961 A1 | 11/1994 |
| WO | 96/00272 A1 | 1/1996 |
| WO | 96/26689 A1 | 9/1996 |
| WO | 96/32907 A1 | 10/1996 |
| WO | 96/34580 A1 | 11/1996 |
| WO | WO 96/41807 A1 | 12/1996 |
| WO | 97/25000 A1 | 7/1997 |
| WO | 97/33534 A1 | 9/1997 |
| WO | WO 97/35575 A1 | 10/1997 |
| WO | WO 98/08463 A1 | 3/1998 |
| WO | 98/13344 A1 | 4/1998 |
| WO | 98/19628 A1 | 5/1998 |
| WO | 98/23228 A1 | 6/1998 |
| WO | 98/23244 A1 | 6/1998 |
| WO | 98/34669 A1 | 8/1998 |
| WO | WO 98/36784 A1 | 8/1998 |
| WO | 98/47447 | 10/1998 |
| WO | 98/56312 A1 | 12/1998 |
| WO | WO 99/55396 A1 | 11/1999 |
| WO | 00/21584 A1 | 4/2000 |
| WO | 00/27445 A1 | 5/2000 |
| WO | 00/32255 A1 | 6/2000 |
| WO | WO 00/38754 A1 | 7/2000 |
| WO | WO 01/87342 A2 | 11/2001 |
| WO | 01/87372 A1 | 11/2001 |
| WO | 01/87373 A1 | 11/2001 |
| WO | WO 01/87376 A1 | 11/2001 |
| WO | 02/26271 A1 | 4/2002 |
| WO | 02/26280 A1 | 4/2002 |
| WO | WO 02/26281 A1 | 4/2002 |
| WO | 03/015664 A1 | 2/2003 |
| WO | 03/022323 A | 3/2003 |
| WO | 03/057218 A1 | 7/2003 |

OTHER PUBLICATIONS

U.S. Appl. No. 10/431,059, filed May 7, 2003, Falotico.

Bauters, C. et al., "Restenosis after coronary angioplasty for rapidly progressive coronary stenosis," European Heart Journal, 1996, 17, 1671–1677.

Dirschinger, J. et al., "Influence of Balloon Pressure During Stent Placement in Native Coronary Arteries on Early and Late Angiographic and Clinical Outcome," Circulation, 1999, 100, 918–923.

Elezi, S. et al., "Vessel Size and Long–Term Outcome After Coronary Stent Placement," Circulation, 1998, 98, 1875–1880.

Erbel, R. et al., "Coronary Artery Stenting Compared With Balloon Angioplasty For Restenosis After Initial Balloon Angioplasty," The New England Journal of Medicine, Dec. 3, 1998, 1672–1678.

Foley, D.P. et al., "Influence of Coronary Vessel Size on Renarrowing Process and Late Angiographic Outcome After Successful Balloon Angioplasty," Circulation, 1994, 90, 1239–1251.

Gibson, C.M. et al., "Lesion–to–lesion independence of restenosis after treatment by conventional angioplasty, stenting, or directional atherectomy. Validation of lesion–based restenosis analysis," Circulation, 1993, 87, 1123–1129.

Gregory, C.R. et al., "Effects of Treatment With Cyclosporine, FK 506, Rapamycin, Mycophenolic Acid, or Deoxyspergualin on Vascular Muscle Proliferation in Vitro and In Vivo," Transplantation Proceedings, Feb. 1993, 25(1), 770–771.

Gregory, C.R. et al., "Rapamycin Inhibits Arterial Intimal Thickening Caused By Both Alloimmune and Mechanical Injury," Transplantation, Jun. 1993, 55, 1409–1418.

Gregory, C.R. et al., Treatment with Rapamycin Blocks Arterial Intimal Thickening Following Mechanical and Alloimmune Injury, Transplantation Proceedings, Feb. 1993, 25(1), 120–121.

Haase, H.D. et al., "Acute and one year follow–up vessel size adapted PTCA using intracoronary ultrasound," European Heart Journal, 1998, 19, 263–272.

Höher, M. et al., "A randomized trial of elective stenting after balloon recanalization of chronic total occlusions," J. Am. Coll. Cardiol., 1993, 34, 722–729.

Kimura, T. et al., "Three–year follow–up after implantation of metallic coronary–artery stents," N. Engl. J. Med., 1996, 334, 561–566.

Kost, J. et al., "Controlled release of bioactive agents," Trends in Biotechnology, 1984, 2(2), 47–51.

Kuntz, R.E. et al., "Defining coronary restenosis. Newer clinical and angiographic paradigms," Circulation, 1993, 88, 1310–1323.

Langer, R., Polymeric Delivery Systems for Controlled Drug Release, Chem. Eng. Commun., 1980, 6, 1–48.

Langer, R. et al., "Polymeric Delivery Systems for Macromolecules: Approaches for Studying In Vivo Release Kinetics and Designing Constant Rate Systems," Am. Chem. Society, 1982, 95–105.

Langer, R. et al., "Polymers for the Sustained Release of Proteins and other Macromolecules," Nature, 1976, 263, 797–800.

Lansky, A. et al., "Randomized Comparison of GR–II Stent and Palmaz–Schatz Stent for Elective Treatment of Coronary Stenoses," Circulation, 2000, 102, 1364–1368.

Marks, A. ,"Attacking Heart Disease with Novel Molecular Tools," NY Acad. Med., 1996, 23–36.

Marx, S. et al., "Bench to Bedside: The Development of Rapamycin and its Application to Stent Restenosis," Circulation, 2001, 104, 852–855.

Marx, S. et al., "Rapamycin–FKBP Inhibits Cell Cycle Regulators of Proliferation in Vascular Smooth Muscle Cells," 1995, 412–417.

Park, S.–W et al., "Randomized Comparison of Coronary Stenting with Optimal Balloon Angioplasty for Treatment of Lesions in Small Coronary Arteries," Eurp. Heart J., 2000, 21, 1785–1789.

Poon, M. et al., "Rapamycin Inhibits Vascular Smooth Muscle Cell Migration," Am. Soc. Clinic. Inv., 1996, 28, 2277–2263.

Murphy, J. et al., "Polymeric Stents: Modern Alchemy or the Future," J. of Invasive Cardio., 1991, 3, 144–148.

Ballard, B. "An Overview of Prolonged Action Drug Dosage Forms," Sustained and Controlled Release Drug Delivery Systems, ED. Joseph R. Robinson, Marcel Dekker, Inc., NY, 1978, Chp. 1, 1–69.

Lee, V. H.–L. et al. "Drug Properties Influencing the Design of Sustained or Controlled Release Drug Delivery Systems," Sustained and Controlled Release Drug Delivery Systems, ED. Joseph R. Robinson, Marcel Dekker, Inc., NY, 1978, Chp. 2, 71–121.

Chien, Y, "Methods to Achieve Sustained Drug Delivery," Sustained and Controlled Release Drug Delivery Systems, ED. Joseph R. Robinson, Marcel Dekker, Inc., NY, 1978, Chp. 4, 211–349.

Chandrasekaran, S. et al., "Methods to Achieve Controlled Drug Delivery," Sustained and Controlled Release Drug Delivery Systems, ED. Joseph R. Robinson, Marcel Dekker, Inc., NY, 1978, Chp. 7, 557–593.

Kwan, K., "Pharmacokinetic Considerations in the Design of Controlled and Sustained Release Drug Delivery Systems," Sustained and Controlled Release Drug Delivery Systems, ED. Joseph R. Robinson, Marcel Dekker, Inc., NY, 1978, Chp. 8, 595–629.

Welling, P. et al., "Multiple Dosing of Sustained Release Systems," Sustained and Controlled Release Drug Delivery Systems, ED. Joseph R. Robinson, Marcel Dekker, Inc., NY, 1978, Chp. 9, 631–716.

Savage, M. et al., "Efficacy of Coronary Stenting Versus Balloon Angioplasty in Small Coronary Arteries," J. Am. Coll. Cardiol., 1998, 31, 307–311.

Sousa, J. et al., "Lack of Neointimal Proliferation After Implantation of Sirolimus–Coated Stents in Human Coronary Arteries: A Quantitative Coronary Angiography and Three–Dimensional Intravascular Ultrasound Study," Circulation, 2000, 0, 54r–57r.

Sousa, J. et al., "Sirolimus–Eluting Stent for the Treatment of In–Stent Restenosis: A Quantitative Coronary Angiography and Three–Dimensional Intravascular Ultrasound Study," Circulation, 2003, 107, 24–27.

Boston Scientific , "Measuring DES Efficacy," www.taxus–stent.com/usa/efficacy.html, pp. 1–3, copyright 2006.

Ullmann's Encyclopedia of Industrial Chemistry, Wolfgang Gerhartz et al. (eds.), 5th completely rev. ed., vol. A11, VCH Publishers, p. 417, 1988.

U.S. Appl. No. 07/819,314, filed Jan. 9, 1992, Morris.

U.S. Appl. No. 08/424,884, filed Apr. 19, 1995, Helmus et al.

U.S. Appl. No. 08/526,273, filed Sep. 11, 1995, Ding.

U.S. Appl. No. 08/730,542, filed Oct. 11, 1996, Helmus.

Abraham, R. T., "Mammalian target of rapamycin: Immunosupressive drugs offer new insight into cell growth regulation," *Progress in Inflammation Research*, 2000, Switzerland.

Alvarado, R. et al., "Evaluation of Polymer–coated Balloon–expandable Stents in Bile Ducts," *Radiology*, 1989, 170, 975–978.

Badimon, J. J. et al., "Inhibitory Effects of Rapamycin on Intimal Hyperplasia After PTCA," *JACC*, Mar. 1998.

Bailey et al., "Polymer Coating of Palmaz–Schatz Stent Attenuates Vascular Spasm after Stent Placement," *Circulation*, 82:III–541 (1990).

Berk, B. C. et al., "Pharmacologic Roles of Heparin and Glucocorticoids to Prevent Restenosis After Coronary Angioplasty," *JACC*, May 1991, 17(6), 111B–117B.

Bertram, P. G. et al., "The 14–3–3 proteins positively regulate rapamycin–sensitive signaling," *Current Biology*, 1998, 8, 1259–1267.

Biomaterials Science (B.D Ratner, Ed.), Academic Press, New York, NY, pp. 228–238, 1996.

Campbell, G. R. et al., "Phenotypic Modulation of Smooth Muscle Cells in Primary Culture, Vascular Smooth Muscle Cells in Culture," *CRC Press*, 1987, 39–55.

Chang, M. W. et al., "Adenovirus–mediated Over–expression of the Cyclin/Cyclin–dependent Kinase inhibitor, p21 inhibits Vascular Smooth Muscle Cell Proliferation and Neointima Formation in the Rat Carotid Artery Model of Balloon Angioplasty," *J. Clin. Invest.*, 195, 96, 2260–2268.

Chung, J. et al., "Rapamycin–FKBP specifically blocks growth–dependent activation of and signaling by the 70 kd S6 protein kinases," *Cell*, Jun. 26, 1992, 69(7), 1227–1236.

Clowes, A. W. et al., "Kinetics of cellular proliferation after arterial injury. IV. Heparin inhibits rat smooth muscle mitogenesis and migration," *Circ. Res.*, 1986, 58(6), 839–845.

Clowes, A. W. et al., Kinetics of Cellular Proliferation after Arterial Injury, *Laboratory Investigation*, 1985, 52(6), 611–616.

Clowes, A. W. et al., "Significance of quiescent smooth muscle migration in the injured rat carotid artery," *Circ Res.* 1985, 56(1), 139–145.

Clowes, A. W., "Suppression by heparin of smooth muscle cell proliferation in injured arteries," *Nature*, 1977, 265(5595), 625–626.

Colburn, M. D. et al., "Dose responsive suppression of myointimal hyperplasia by dexamethasone," *J. Vasc. Surg.*, 1992, 15, 510–518.

Currier, J. W. et al., "Colchicine Inhibits Restenosis After Iliac Angioplasty in the Atherosclerotic Rabbit," *Circ.*, 1989, 80(4), 11–66 (Abstract No. 0263).

Farb, A. et al., "Vascular smooth muscle cell cytotoxicity and sustained inhibition of neointimal formation by fibroblast growth factor 2–saporin fusion protein," *Circ. Res.*, 1997, 80, 542–550.

Ferns, G. A. A. et al., "Inhibition of Neointimal Smooth Muscle Accumulation After Angioplasty by an Antibody to PDGF," *Science*, 1991, 253, 1129–1132.

Fischman, D. L. et al., "A Randomized Comparison of Coronary–Stent Placement and Balloon Angioplasty in the Treatment of Coronary Artery Disease," *N. Eng. J. Med.*, Aug. 25, 1994, 331(8), 496–501.

Franklin, S. M. et al., "Pharmacologic prevention of restenosis after coronary angioplasty: review of the randomized clinical trials," *Coronary Artery Disease* Mar. 1993, 4(3), 232–242.

Fukuyama, J. et al., "Tranilast suppresses the vascular intimal hyperplasia after balloon injury in rabbits fed on a high–cholesterol diet," *Eur. J. Pharmacol.*, 1996, 318, 327–332.

Gregory, C. R. et al., "Rapamycin Inhibits Arterial Intimal Thickening Caused by Both Alloimmune and Mechanical Injury," *Transplantation*, Jun. 1993, 55(6), 1409–1418.

Gregory, C. R. et al, "Treatment with Rapamycin and Mycophenolic Acid Reduces Arterial Intimal Thickening Produced by Mechanical Injury and Allows Endothelial Replacement," *Transplantation*, Mar. 15, 1995, 59(5), 655–661.

Guyton, J. R. et al., "Inhibition of rat arterial smooth muscle cell proliferation by heparin. In vivo studies with anticoagulant and nonanticoagulant heparin," *Circ. Res.*, 1980, 46, 625–634.

Hansson, G. K. et al., "Interferon–γ Inhibits Arterial Stenosis After Injury," *Circ.*, 1991, 84, 1266–1272.

Hashemolhosseini, S. et al., "Rapamycin Inhibition of the G1 to S Transition Is Mediated by Effects on Cyclin D1 mRNA and Protein Stability," *J Biol Chem*, Jun. 5, 1998, 273, 14424–14429.

Jonasson, J. et al., "Cyclosporin A inhibits smooth muscle proliferation in the vascular response to injury," *Proc. Natl., Acad. Sci.*, 1988, 85, 2303–2306.

Kuhnt, M. et al., "Microbial Conversion of Rapamycin," *Enzyme and Microbial Technology*, 1997, 21, 405–412.

Lange, R. A. MD et al., "Restenosis After Coronary Balloon Angioplasty," *Annu. Rev. Med.*, 1991, 42, 127–132.

Liu, M. W. et al., "Trapidil in Preventing Restenosis After Balloon Angioplasty in the Atherosclerotic Rabbit," *Circ.*, 1990, 81, 1089–1093.

Liu, M. W., MD et al., "Restenosis After Coronary Angioplasty Potential Biologic Determinants and Role of Intimal Hyperplasia," *Circulation*, 1989, 79, 1374–1387.

Lundergan, C. F. et al., "Peptide inhibition of Myointimal Proliferation by Angiopeptin, a Somatostatin Analogue," *JACC*, May 1991, 17(6), 132B–136B.

Majesky, M. W. et al., "Heparin regulates smooth muscle S phase entry in the injured rat carotid artery," *Circ. Res.*, 1987, 61, 296–300.

Marx, S. O. et al., "Rapamycin–FKBP Inhibits Cell Cycle Regulators of Proliferation in Vascular Smooth Muscle Cells," *Circ. Res.*, 1995, 76, 412–417.

Nemecek, G. M. et al., "Terbinafine Inhibits the Mitogenic Response to Platelet–Derived Growth Factor in Vitro and Neoinimal Proliferation in Vivo," *J. Pharmacol. Exp. Thera.*, 1989, 248, 1167–1174.

Okada, T. et al., "Localized Release of Perivascular Heparin Inhibits Intimal Proliferation after Endothelial Injury without Systemic Anticoagulation," *Neurosurgery*, 1989, 25, 892–898.

Poon, M. et al., "Rapamycin Inhibits Vascular Smooth Muscle Cell Migration," *J. Clin Invest.*, Nov. 1996, 98(10), 2277–2283.

Popma, J. J. et al., "Clinical trials of restenosis after coronary angioplasty," *Circulation*, Sep. 1991, 84(3), 1426–1436.

Powell, J. S. et al., "Inhibitors of Angiotensin–Converting Enzyme Prevent Myointimal Proliferation After Vascular Injury," *Science*, 1989, 245, 186–188.

Rensing, B. J. et al., Coronary restenosis elimination with a sirolimus eluting stent, *European Heart Journal*, 2001, 22, 2125–2130.

Rodeck, C. et al., "Methods for the Transcervical Collection of Fetal Cells During the First Trimester of Pregnancy," *Prenatal Diagnosis*, 1995, 15, 933–942.

Ruef, J. MD, et al., "Flavopiridol Inhibits Muscle Cell Proliferation In Vitro and Neointimal Formation In Vivo After Carotid Injury in the Rat," From the Division of Cardiology and Sealy Center for Molecular Cardiology, University of Texas Medical Branch, Galveston; Accepted Apr. 9, 1999; *Circulation* Aug. 10, 1999, pp. 659–665.

Serruys, P. W. et al., "A comparison of balloon–expandable–stent implantation with balloon angioplasty in patients with coronary artery disease," *N Engl J Med*, Aug. 25, 1994; 331(8), 489–495.

Serruys, P. W. et al., "Evaluation of ketanserin in the prevention of restenosis after percutaneous transluminal coronary angioplasty. A multicenter randomized double–blind placebo–controlled trial," *Circulation*, Oct. 1993; 88(4 Pt 1), 1588–1601.

Serruys, P. W. et al., "Heparin–coated Palmaz–Schatz stents in human coronary arteries. Early outcome of the Benestent–II Pilot Study," *Circulation*, Feb. 1, 1996; 93(3), 412–422.

Siekierka, J. J., "Probing T–Cell Signal Transduction Pathways with the Immunosupressive Drugs, FK–506 and Rapamycin," *Immunologic Research*, 1994, 13, 110–116.

Sigwart, et al., "Intravascular Stents to Prevent Occlusion and Restenosis After Transluminal Angioplasty," *N. Engl. J. Med.*, Mar. 19, 1987, 316, 701–706.

Simons, M. et al., "Antisense c–*myb* oligonucleotides inhibit intimal arterial smooth muscle cell accumulation in vivo," *Nature*, 1992, 359, 67–70.

Snow, A. D. et al., "Heparin modulates the composition of the extracellular matrix domain surrounding arterial smooth muscle cells," *Am J. Pathol.*, 1990, 137, 313–330.

Sollott, S. J. et al., "Taxol Inhibits Neointimal Smooth Muscle Cell Accumulation after Angioplasty in the Rat," *J. Clin. Invest.*, 1995, 95, 1869–1876.

van Der Giessen, et al., "Self–expandable Mesh Stents: an Experimental Study Comparing Polymer Coated and Uncoated Wallstent Stents in the Coronary Circulation of Pigs," *Circulation* 1990, 82 (suppl. III):III–542.

van Der Giessen, W. J. et al., "Coronary stenting with polymer–coated and uncoated self–expanding endoprostheses in pigs," Coron. Art. Disease 1992; 3, 631–640.

Vasey, C. G. et al., "Clinical Cardiology: Stress Echo and Coronary Flow", , *Circulation*, Oct. 1989, 80(4) Supplement II, II–66.

Weinberger, J. et al., "Intracoronary irradiation: dose response for the prevention of restenosis in swine," *Int. J. Rad. Onc. Biol. Phys.*, 1996, 36, 767–775.

SOLEF® PVDF Copolymer ($VF_2$—HFP) Technical Data Sheets, 2000, 6 pages.

VITON® PVDF Copolymer ($VF_2$—HFP) Marerial Safety Data Sheet, 2006, 7 pages.

VITON® Technical Information, Rev. 6, Nov. 2005, 16 pages.

Wright et al., Percutaneous Endovascular Stent: An Experimental Study (Abstract), RSNA Meeting (Nov. 28, 1984).

Palmaz et al., Article: "Normal and Stenotic Renal Arteries: Experimental Balloon Expandable Intraluminal Stenting", Radiology, Sep. 1987 (AVE 84).

Julio C. Palmaz, Article: "Expandable vascular endoprosthesis." (AVE 132).

Duprat et. al., Article: Flexible Balloon–Expandable Stent for Small Vessels Duprat et. al. Radiology, vol. 162, pp. 276–278, 1987. (AVE 134).

Coons et. al. Article: "Large–Bore, Long Biliary Endoprosthesis (Biliary Stents for Improved Drainage," Radiology, vol. 148, pp. 89–94, 1983. (AVE 143).

Honickman et al., Article: "Malpositioned Biliary Endoprosthesis, Technical Developments And Instrumentation," vol. 144, No. 2., 1982. (AVE 144).

Harries–Jones, et al., Article: "Repositioning of Biliary Endoprosthesis with Gruntzig Balloon Catheters," AJR, vol. 138, pp. 771–772, 1982. (AVE 153).

Charnsangavej et al., Article "Stenosis of the Vena Cava: Preliminary Assessment of Treatment with Expandable Metallic Stents," Radiology, vol. 161, pp. 295–298, 1986. (AVE 359).

Wallace, M. J. et al., Article "Tracheobronchial Tree: Expandable Metallic Stents Used in Experimental and Clinical Applications," Radiology, vol. 158, pp. 309–312, 1986. (AVE 364).

T. Yoshioka, et al., AIR Article: "Self–Expanding Endovascular Graft: An Experimental Study in Dogs", vol. 151, pp. 673–676, 1988. (AVE 438).

Palmaz, J. C. et al., Article: "Expandable Intraluminal Vascular Graft: A Feasibility Study," Surgery, vol. 99, pp. 199–205, 1986. (AVE 461).

Lawrence et al., Article: "Percutaneous Endovescular Graft: Experimental Evaluation." Radiology, vol. 163, pp. 357–360, 1987. (AVE 671).

Palmaz et al., Article: Expandable Intraluminal Graft: A Preliminary Study, Nov. 17–22, 1985, Radiology, vol. 156, pp. 73–77, 1985. (AVE 1224).

Fallone et al., "Elastic Characteristics of the Self–Expanding Metallic Stents," Investigative Radiology, vol. 23, pp. 370–376, 1988. (AVE 1953).

Palmaz Paper Entitled "Research Project Expandable Vascular Endoprosthesis" May 18, 1983.

Rousseau , et al., Publication: "Percutaneous Vascular Stent: Experimental Studies & Preliminary Clinical Results in Peripheral Arterial Diseases," in Inter. Angio, vol. 6, 153–161,1987. (AVE 3301).

Rousseau , et al., Publication: "Self–Expanding Endovascular Prostesis: An Experimental Study," Radiology, vol. 164, pp. 709–714, 1987. (AVE 3303).

Wallace, et al., Article: "Tracheobronchial Tree: Expandable Metallic Stents Used in Experimental and Clinical Applications," Radiology, vol. 58, pp. 309–312, 1986. (DBX 2938).

Palmaz et al., Article: "Expandable Intraluminal Graft: A Preliminary Study," Radiology, vol. 156, pp. 73–77, Nov. 17–22, 1985 (DBX 4595).

Program for the 12th Annual Course on Diagnostic Angiography and Interventional Radiology Mar. 23–26, 1987 sponsored by The Society of Cardiovascular and Interventional Radiology (DBX 6235).

Duprat et al., Article: "Flexible Balloon–Expandable Stent For Small Vessels," Radiology, vol. 168, pp. 276–278, 1987 (PX 82).

Drawing Sent to Bodic on Mar. 17, 1986 (PX 374).

Charnsangavej, et al., Article: "Stenosis of The Vena Cava Prelimimnary Assessment of Treatment with expandable Metallic Stents," Radiology, vol. 161, No. 2, pp. 295–298 with attached photographs, 1986. (API 72).

J. Palmaz: The Current Status of Vascular Prostheses, published by SCIR in the Twelfth Annual Course on Diagnostic Angiography And Interventional Radiology Mar. 23–26, 1987. (API 73).

Article: Wallace, et al., Tracheobronchial Tree: Expandable Metallic Stents Used in Experimental and Clinical Applications Work In Progress, Radiology, vol. 158, pp. 309–312. (API 295).

Wallace, et al., Article: "Tracheobronchial Tree: Expandable Metallic Stents Used in Experimental and Clinical Applications' Work In Progress," Radiology, vol. 158, pp. 309–312, 1986. (Exhibit 165).

Charnsangavej, et al., Article: "Stenosis of The Vena Cava Prelimimnary Assessment of Treatment with expandable Metallic Stents," Radiology, vol. 161, No. 2, pp. 295–298 with attached photographs, 1986! (Exhibit 167).

David D. Lawrence et al., Publication: Percutaneous Endo-yascular Graft: Experimental Evaluation[1], Radiology, pp. 163, 357–360, 1987. (Exhibit 173).

Charles E. Putnam, M.D., Cover and article from "Investigative Radiology", vol. 23. No. 5, May 1988. (Exhibit 177).

Robert N. Berk, Cover and article from "American Journal of Roentology", pp. 673–676, 1988. (Exhibit 178).

Yoshioka et al., Article: "Self–Expanding Endovascular Graft: An Experimental Study in Dogs" AJR, vol. 151, pp. 673–676, 1988. (PX 100).

Palmaz, et al., Article: Expandable Intraluminal Graft: A Preliminary Study Work in Progress[1], Radiology, vol. 156, No. 1, pp. 73–77, 1985. (PX 101).

Charnsangavej et al., Article: "Stenosis of the Vena Cave: Preliminary Assessment of Treatment with Expandable Metallic Stents," Radiology, vol. 161, pp. 295–298, 1986. (PX 143).

Wallace, et al., Article: Tracheobronchial Tree: Expandable Metallic Stents Used in Experimental and Clinical Applications Work in Progress[1], Radiology, vol. 158, pp. 309–312, 1986. (PX 144)

Gina Kolata, News Article: NY Times, "Devices That Opens Clogged Arteries Gets a Falling Grade in a New Study", pp. 16–18, Jan. 3, 1991. (PX 186).

Duprat, et al., Article: "Flexible Balloon– Expanded Stent for Small Vessels Work in Progress[1]" Radiology, vol. 162, pp. 276–278, 1987. (PX 207).

Kuntz, et al., Article: Clinical Cardiology Frontiers: "Defining Coronary Restenosis, Newer Clinical and Angiographic Paradigms", Circulation, Sep. 1993, vol. 88, No. 3, pp. 1310–1323. (PX 854).

Drawing of Spiral Stent (sent to Bodic Mar. 17, 1986). (PX2933).

Wright et al., Article: "Percutaneous Endovascular Stents: An Experimental Evaluation," Radiology, vol. 156, pp. 69–72, 1985. (PX 3093).

Charnsangavej et al., Article: "A New Expandable Metallic Stent for Dilation of Stenotic Tubular Structures: Experimental and Clinical Evaluation," Houston Medical Journal, vol. 3, pp. 41–51, Jun. 1987. (PX 3207).

Mullins et al., Article: "Implantation of balloon–expandable intravascular grafts by catherization in pulmonary arteries and systemic veins," Circulation, vol. 77, No. 1, pp. 188–199,1988. (PX4049).

Schatz et al., Article: "Intravascular Stents for Angioplasty," Cardio, 1997. (PX 4050).

Schatz et al., Article: "New Technology in Angioplasty Balloon–Expandable Intravascular Stents, New Developments in Medicine," vol. 2, No. 2 pp. 59–75, 1987. (PX4051).

Richard A. Schatz, Article: "Introduction to Intravascular Stents," Cardiology Clinics, vol. 6, No. 3, pp. 357–372, 1988. (PX 4052).

Richard A. Schatz, Article: "A View of Vascular Stents," Circulation, vol. 79, No. 2, pp. 445–457, 1989. (PX4053).

Wang et al., Article: "An Update on Coronary Stents," Cardio, pp. 177–186, 1992. (PX 4054).

Richard A. Schatz, Article: "New Technology in Angioplasty: Balloon–Expandable Starts," Medicamundi, vol. 33, No. 3, pp. 1 12–1 16, 1988. (PX 4055).

Articulated, Balloon—Expandable Stents, (DBX 7159).

J. Rosch et al., Experimental Intrahepatic Portacaval Anastomosis: Use of Expandable Gianturco Stents, Radiology, vol. 162, pp. 481–485, 1987.

J. Rosch et al., Modified Gianturco Expandable Wire Stents In Experimental and Clinical Use, Ann Radiol, vol. 31, No. 2, pp. 100–103, 1987.

J. Rosch et al., Gianturco Expandable Stents In the Treatment of Superior Vena Cava Syndrome Recurring After Vena Cava Syndrome Recurring After Maximum–Tolerance Radiation, Cancer, vol. 60, pp. 1243–1246, 1987.

J.E. Gordon, Structures or Why Things Don't Fall Down, Penguin Books, pp. 45–59,132–148,210–244,377–383.

Maass et al., Radiological Follow–up of Transluminallly Inserted Vascular Endoprostheses: An Experimental Study Using Expanding Spirals, Radiology, vol. 152, pp. 659–663, 1984.

Papanicolaou et al., Insertion of a Biliary Endoprosthesis Using A Balloon Dilatation Catheter, Gastrointest Radiology, vol. 10, pp. 394–396, 1985.

Palmaz et al., Atheroscierotic Rabbit Aortas: Expandable Intraluminal Grafting, Radiology, vol. 168, pp. 723–726, 1986.

Palmaz, The Current Status of Vascular Prostheses; Rosch et al., Gianturco, Expandable Stents in Experimental and Clinical Use, SCIVR, pp. 1 18–124, 1987.

Rosch et al., Abstract: Modified Gianturco Expandable Wire Stents in Experimental and Clinical Use, CIRSE, Porto Cervo, Sardinia, May 25–29, 1987.

Rosch et al., Gianturco Expandable Wire Stents in the Treatment of Superior Vena Cava Syndrome Recurring After Maximum–Tolerance Radiation, Cancer, vol. 60, pp. 1243–1246, 1987.

Mirich et al., Percutaneously Placed Endovascular Grafts for Aortic Aneurysms: Feasibility Study, Radiology, vol. 170, pp. 1033–1037, 1989.

Dotter, Transluminally–placed Coilspring Endarterial Tube Grafts, Investigative Radiology, vol. 4, Sep.–Oct., pp. 329–332, 1969.

Palmaz et al., Abstract: Expandable Intraluminal Graft: A Preliminary Study, Radiology, vol. 153 (P), Nov. 1983: 70th Scientific Assembly and Annual Meeting.

Cragg et al, Nonsurgical Placement of Arterial Endoprostheses: A New Technique Using Nitinol Wire, Radiology, vol. 147, pp. 261–263, Apr. 1983.

J. Rosch et al., Gianturco Expandable Stents in Experimental and Clinical Use, Program: "Twelfth Annual Course on Diagnostic Angiography and Interventional Radiology" (Society of Cardiovascular and Interventional Radiology, Pittsburgh, PA), Mar. 23–26, 1987 (the second Monofilament Article).

Uchida et al., Modifications of Gianturco Expandable Wire Stents, AIR, vol. 150, pp. 1185–1187,1988.

Palmaz, Balloon–Expandable Intravascular Stent, AJR, vol. 1510, pp. 1263–1269.

J. Rosch et al., Abstract, Expandable Gianturco–Type Wire Stents in Experimental Intrahepatic Portacaval Shunts, Program: "72nd Scientific Assembly and Annual Meeting of the Radiological Society of North America", Nov. 30–Dec. 5, 1986, Radiology, vol. 161, pp. 40–41, 1986.

Wu et al., Silicone–covered self–expanding metallic stents for the palliation of malignant esophageal obstruction and esophagorespiratory fistulas: experience in 32 patients and a review of the literature, *Gastrointestinal Endoscopy*, 1994, pp. 22–33, vol. 40, No. 1, Portland Oregon.

Binmoeller, et al., Silicone–Covered Expandable Metallic Stents in the Esophagus: An Experimental Study, Endoscopy, 1992, pp. 416–420, vol. 24, Georg Thieme Verlag Stuttgart New York.

Rhine, Polymers for Sustained Macromolecule Release: Procedures to Fabricate Reproducible Delivery Systems and Control Release Kinetics, *Journal of Pharmaceutical Sciences*, 1 980, pp. 265–270, vol. 69, No. 3.

Langer et al., Controlled Release of Macromolecules From Polymers, *Biomedical Polymers Polymeric Materials and Pharmaceuticals for Biomedical Use*, 1980, pp. 112–137, Academic Press, Inc., New York, NY.

Langer et al., Applications of Polymeric Delivery Systems for Macromolecules and Factors Controlling Release Kinetics.

Rhine et al., A Method to Achieve Zero–Order Release Kinetics From Polymer Matric Drug Delivery Systems, pp. 67–72.

Langer et al., Polymers for the Sustained Release of Macromolecules: Controlled and Magnetically Modulated Systems, *Better Therapy With Existing Drugs: New Uses and Delivery Systems*; 1981, pp. 179–216, Merck Sharp & Dohme International, Rahway, NJ.

Hsieh, et al., Zero–Order Controlled–Release Polymer Matrices for Micro–and–Macromolecules, *Journal of Pharmaceutical Sciences*, 1983 pp. 17–22, vol. 72, No. 1.

Brown et al., In Vivo and In Vitro Release of Macromolecules from Polymeric Drug Delivery Systems, *Journal of Pharmaceutical Sciences*, 1983, pp. 1181–1185, vol. 72, No. 10.

Langer, Implantable Controlled Release Systems, *Pharmac. Ther.*, 1983, pp. 35–51, vol. 21, printed in Great Britain.

Kost et al., Controlled Release of Bioactive Agents, *Trends in Biotechnology*, 1984, pp. 47–51, vol. 2, No. 2, Elsevier BV Amsterdam.

Bawa et al., An Explanation for the Controlled Release of Macromolecules from Polymers, *Journal of Controlled Release*, 1985, pp. 259–267, vol. 1 Elsevier Science BV Amsterdam.

Leong et al., Polymeric Controlled drug delivery, 1987, pp. 199–233, vol. 1/3, Elsevier Science Publishers BV Amsterdam.

Langer, Polymeric Delivery Systems, *Targeting of Drugs 2 Optimization Strategies*, 1989, pp. 165–174, Plenum Press, New York and London.

Langer, Biomaterials in Controlled Drug Delivery; New Perspectives from Biotechnological Advances; *Pharmaceutical Technology*, 1989, pp. 18, 23–24, 26, 28, 30.

Langer, Controlled Release Systems, pp. 115–124.

Laurencin et al., Polymeric Controlled Release Systems: New Methods for Drug Delivery, *Clinics in Laboratory Medicine*, 1987, pp. 301–323, vol. 7, No. 2, WB Saunders Company, Philadelphia.

Langer, Biopolymers in Controlled Release Systems, *Polymeric Biomaterials*, pp. 161–169.

Tsong–Pin Hsu et al., Polymers for the Controlled Release of Macromolecules: Effect of Molecular Weight of Ethylene–vinyl Acetate Copolymer, *Journal of Biomedical Materials Research*, 1985, pp. 445–460, vol. 19.

Langer, Polymers and Drug Delivery Systems, *Long–Acting Contraceptive Delivery Systems*, 1983, pp. 23–32, Harper & Row, Philadelphia, PA.

Langer, New Drug Delivery Systems: What the Clinician Can Expect, *Drug Therapy*, 1983, pp. 217–231.

Langer, et al., Chemical and Physical Structure of Polymers as Carriers for Controlled Release of Bioactive Agents: A Review, *Rev. Macromol. Chem. Phys.*, 1983, pp. 61–126.

Langer, Polymer Delivery Systems for Controlled Drug Release, *Chem. Eng. Commun*. 1980, pp. 1—48–vol. 6, Gordon and Breach Science Publishers, Inc. USA.

Langer, et al., Biocompatibility of Polymeric Delivery Systems for Macomolecules, *Journal of Biomedical Materials Research*, 1981, pp. 267–277, vol. 15.

Langer, Controlled Release: A New Approach to Drug Delivery, *Technology Review*, 1981, pp. 26–34.

Langer, et al., Sustained Release of Macromolecules from Polymers, *Polymeric Delivery Systems*, pp. 175–196, Gordon and Breach Science Publishers, New York.

Langer, Polymers for the Sustained Release of Proteins and other Macromolecules, *Nature*, 1976, pp. 797, 263, 799–800, vol. 263, No. 5580.

Baker, et al., Controlled Release: Mechanisms and Rates (1974).

Hanson, et al., In Vivo Evaluation of Artificial Surfaces with a Nonhum Primate Model of Arterial Thrombosis,/ *Lab Clin. Med.*, Feb. 1980, pp. 289–304.

Baker, Controlled Release of Biologically Active Agents (1987) pp. 1–275.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3 and 5 are cancelled.

Claim 4 is determined to be patentable as amended.

New claims 6-9 are added and determined to be patentable.

4. [The] *An* implantable medical device [of claim 1, wherein said film further comprises] *comprising a metallic stent and a biocompatible film coating effective to provide an inert surface to be in contact with body tissue of a mammal upon implantation of said device in said mammal, said film coating comprising* a polyfluoro copolymer comprising about 85 weight percent of polymerized residue of vinylidenefluoride and about 15 weight percent of polymerized residue of hexafluoropropylene mixed with effective amounts of a therapeutic and/or pharmaceutical agent.

*6. The implantable medical device of claim 4, wherein said polyfluoro copolymer comprises 85.5 weight percent vinylidenefluoride copolymerized with 14.5 weight percent hexafluoropropylene.*

*7. The implantable medical device according to any one of the preceding claims wherein said therapeutic and/or pharmaceutical agent is an immunosuppressive or a mTOR inhibitor.*

*8. The implantable medical device according to claim 7 wherein said film coating is heated to a maximum temperature of less than about 100° C.*

*9. The implantable medical device according to claim 8 wherein said film coating is heated to a maximum temperature of less than about 65° C.*

* * * * *

(12) INTER PARTES REEXAMINATION CERTIFICATE (1294th)
United States Patent
Llanos et al.

(10) Number: US 6,746,773 C2
(45) Certificate Issued: Jun. 28, 2016

(54) COATINGS FOR MEDICAL DEVICES

(75) Inventors: Gerard H. Llanos, Stewartsville, NJ (US); Mark B. Roller, North Brunswick, NJ (US); Angelo Scopelianos, Whitehouse Station, NJ (US); Robert Falotico, Belle Mead, NJ (US)

(73) Assignee: ETHICON, INC., Somerville, NJ (US)

Reexamination Request:
No. 95/000,567, Aug. 23, 2010

Reexamination Certificate for:
Patent No.: 6,746,773
Issued: Jun. 8, 2004
Appl. No.: 09/962,292
Filed: Sep. 25, 2001

Reexamination Certificate C1 6,746,773 issued Jul. 13, 2010

Related U.S. Application Data

(63) Continuation-in-part of application No. 09/675,882, filed on Sep. 29, 2000, now abandoned.

(51) Int. Cl.
| | |
|---|---|
| *A61B 17/11* | (2006.01) |
| *A61B 17/115* | (2006.01) |
| *A61B 17/54* | (2006.01) |
| *A61F 2/06* | (2013.01) |
| *A61L 17/14* | (2006.01) |
| *A61L 17/00* | (2006.01) |
| *A61L 27/00* | (2006.01) |
| *A61L 29/08* | (2006.01) |
| *A61L 27/34* | (2006.01) |
| *A61L 29/00* | (2006.01) |
| *A61L 31/16* | (2006.01) |
| *A61B 17/03* | (2006.01) |
| *A61L 31/14* | (2006.01) |
| *A61L 31/10* | (2006.01) |
| *A61B 17/064* | (2006.01) |
| *A61L 31/08* | (2006.01) |
| *A61F 2/91* | (2013.01) |
| *A61F 2/915* | (2013.01) |
| *A61K 31/436* | (2006.01) |
| *A61K 31/727* | (2006.01) |
| *A61K 45/06* | (2006.01) |
| *A61L 31/02* | (2006.01) |
| *A61L 31/18* | (2006.01) |
| *C08L 27/16* | (2006.01) |
| *C08L 27/12* | (2006.01) |
| *C08L 27/14* | (2006.01) |
| *A61F 2/00* | (2006.01) |
| *A61B 17/00* | (2006.01) |
| *A61B 17/04* | (2006.01) |
| *A61B 17/06* | (2006.01) |
| *A61F 2/30* | (2006.01) |

(52) U.S. Cl.
CPC ............ *A61B 17/0644* (2013.01); *A61B 17/11* (2013.01); *A61B 17/115* (2013.01); *A61B 17/54* (2013.01); *A61F 2/91* (2013.01); *A61F 2/915* (2013.01); *A61K 31/436* (2013.01); *A61K 31/727* (2013.01); *A61K 45/06* (2013.01); *A61L 17/145* (2013.01); *A61L 27/34* (2013.01); *A61L 29/085* (2013.01); *A61L 31/022* (2013.01); *A61L 31/10* (2013.01); *A61L 31/18* (2013.01); *C08L 27/12* (2013.01); *C08L 27/14* (2013.01); *C08L 27/16* (2013.01); *A61B 17/00491* (2013.01); *A61B 17/0469* (2013.01); *A61B 2017/06028* (2013.01); *A61F 2/064* (2013.01); *A61F 2002/3008* (2013.01); *A61F 2002/91533* (2013.01); *A61F 2002/91558* (2013.01); *A61F 2250/0067* (2013.01); *A61F 2250/0098* (2013.01); *A61F 2310/0097* (2013.01); *A61F 2310/00976* (2013.01); *A61K 2300/00* (2013.01); *Y10T 428/3154* (2015.04)

(58) Field of Classification Search
None
See application file for complete search history.

(56) References Cited

To view the complete listing of prior art documents cited during the proceeding for Reexamination Control Number 95/000,567, please refer to the USPTO's public Patent Application Information Retrieval (PAIR) system under the Display References tab.

*Primary Examiner* — Dwayne Jones

(57) ABSTRACT

The present invention includes biocompatible coatings and films for use on implantable medical devices and medical devices containing such coatings and films applied to a surface thereof, which coatings/films are present on the device in an amount effective to provide an inert surface to be in contact with body tissue of a mammal upon implantation of the device in the mammal, and contain a film-forming polyfluoro copolymer containing the polymerized residue of a moiety selected from the group consisting of vinylidenefluoride and tetrafluoroethylene copolymerized with a second moiety other than the first moiety, wherein the relative amounts of the polymerized residue of the first and second moieties are effective to provide the coating and films with properties effective for use in coating implantable med devices.

INTER PARTES REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-3 and 5 were previously cancelled.
Claims 4 and 6-9 are cancelled.

* * * * *